(12) United States Patent
Lewis et al.

(10) Patent No.: US 8,394,330 B1
(45) Date of Patent: Mar. 12, 2013

(54) CONDUCTIVE ORGANIC SENSORS, ARRAYS AND METHODS OF USE

(75) Inventors: Nathan S. Lewis, La Canada, CA (US); Carol Lewis, La Canada, CA (US); Robert Grubbs, South Pasadena, CA (US); Gregory Allen Sotzing, Willington, CT (US)

(73) Assignee: The California Institute of Technology, Pasadena, CA (US)

( * ) Notice: Subject to any disclaimer, the term of this patent is extended or adjusted under 35 U.S.C. 154(b) by 0 days.

(21) Appl. No.: 09/409,644

(22) Filed: Oct. 1, 1999

Related U.S. Application Data

(60) Provisional application No. 60/102,817, filed on Oct. 2, 1998, provisional application No. 60/143,202, filed on Jul. 9, 1999.

(51) Int. Cl.
G01N 27/27 (2006.01)
G01N 27/04 (2006.01)
G01N 27/26 (2006.01)
G01N 27/49 (2006.01)

(52) U.S. Cl. ......... 422/98; 73/23.3; 73/23.31; 73/23.34; 73/29.01; 73/31.01; 73/31.05; 73/335.05; 204/403.01; 204/403.03; 204/403.13; 204/403.15; 204/431; 422/88; 422/90

(58) Field of Classification Search ............ 422/88, 422/90, 98; 204/403; 73/23.2, 23.3, 23.31, 73/23.34, 29.01, 31.01, 31.05, 335.05
See application file for complete search history.

(56) References Cited

U.S. PATENT DOCUMENTS

| | | | |
|---|---|---|---|
| 4,225,410 A * | 9/1980 | Pace ........................ 204/195 R |
| 4,349,664 A * | 9/1982 | Matsumura et al. .......... 528/291 |
| 4,453,126 A | 6/1984 | Volgyesi |
| 4,636,767 A * | 1/1987 | Barger et al. .................... 338/34 |
| 4,674,320 A | 6/1987 | Hirschfeld ......................... 73/23 |
| 4,731,311 A * | 3/1988 | Suzuki et al. ................. 429/213 |
| 4,737,112 A | 4/1988 | Jin et al. |
| 4,772,559 A | 9/1988 | Preti et al. |
| 4,911,801 A * | 3/1990 | Pons ........................... 204/59 R |
| 4,923,739 A | 5/1990 | Jin et al. |
| 4,927,502 A | 5/1990 | Reading et al. |
| 4,946,562 A | 8/1990 | Guruswamy |
| 4,980,541 A | 12/1990 | Shafe et al. |
| 5,045,285 A * | 9/1991 | Kolesar, Jr. ..................... 422/98 |
| 5,215,820 A * | 6/1993 | Hosokawa et al. ........... 428/403 |
| 5,217,692 A * | 6/1993 | Rump et al. ..................... 422/98 |
| 5,225,110 A * | 7/1993 | Kathirgamanathan ........ 252/512 |
| 5,286,414 A | 2/1994 | Kampf et al. |
| 5,298,783 A | 3/1994 | Wu |

(Continued)

FOREIGN PATENT DOCUMENTS

| | | | |
|---|---|---|---|
| DE | 3728452 | * | 3/1989 |
| EP | 0 597 452 A1 | | 5/1994 |

(Continued)

OTHER PUBLICATIONS

K. Rajeshwar et al, Polymer Preprints 1994, 35, 234-235.*

(Continued)

*Primary Examiner* — Arlen Soderquist
(74) *Attorney, Agent, or Firm* — Joseph R. Baker, Jr.; Gavrilovich Dodd & Lindsey LLP

(57) ABSTRACT

The present invention provides a class of sensors prepared from regions of conducting organic materials and conducting materials that show an increase sensitivity detection limit for amines. The present class of sensors have applications in the detection of spoiled food products and in testing for diseases, such as cholera and lung cancer, which have amines as biomarkers.

52 Claims, 18 Drawing Sheets

U.S. PATENT DOCUMENTS

| | | | |
|---|---|---|---|
| 5,302,274 A | | 4/1994 | Tomantachger et al. |
| 5,338,430 A | * | 8/1994 | Parsonage et al. ............ 204/412 |
| 5,352,574 A | * | 10/1994 | Guiseppi-Elie .................... 435/4 |
| 5,366,766 A | * | 11/1994 | Sekiguchi et al. ......... 427/255.4 |
| 5,407,699 A | * | 4/1995 | Myers ........................... 427/121 |
| 5,415,893 A | * | 5/1995 | Wiersma et al. ........... 427/385.5 |
| 5,417,100 A | | 5/1995 | Miller et al. |
| 5,425,869 A | | 6/1995 | Noding et al. |
| 5,451,920 A | | 9/1995 | Hoffheins et al. |
| 5,466,348 A | | 11/1995 | Holm-Kennedy ......... 204/153.1 |
| 5,498,372 A | * | 3/1996 | Hedges ......................... 252/511 |
| 5,505,093 A | | 4/1996 | Giedd et al. |
| 5,512,882 A | | 4/1996 | Stetter et al. |
| 5,519,147 A | | 5/1996 | Swager et al. |
| 5,536,473 A | | 7/1996 | Monkman et al. |
| 5,571,401 A | | 11/1996 | Lewis et al. ................... 205/787 |
| 5,674,752 A | | 10/1997 | Buckley et al. |
| 5,677,662 A | | 10/1997 | Bresolin et al. |
| 5,698,089 A | | 12/1997 | Lewis et al. ................... 205/787 |
| 5,698,771 A | | 12/1997 | Shields et al. |
| 5,705,265 A | | 1/1998 | Clough et al. |
| 5,742,223 A | | 4/1998 | Simendinger, III et al. |
| 5,756,879 A | * | 5/1998 | Yamagishi et al. .......... 73/28.01 |
| 5,766,934 A | | 6/1998 | Guiseppi-Elie |
| 5,788,833 A | | 8/1998 | Lewis et al. ................... 205/787 |
| 5,801,297 A | * | 9/1998 | Mifsud et al. |
| 5,804,100 A | | 9/1998 | Angelopoulos et al. |
| 5,807,701 A | | 9/1998 | Payne et al. |
| 5,832,411 A | | 11/1998 | Schatzmann et al. |
| 5,841,021 A | * | 11/1998 | De Castro et al. ............. 73/23.2 |
| 5,846,744 A | | 12/1998 | Athey et al. |
| 5,869,007 A | * | 2/1999 | Jang ........................... 422/82.02 |
| 5,876,577 A | | 3/1999 | McAleer et al. |
| 5,879,827 A | | 3/1999 | Debe et al. |
| 5,926,360 A | * | 7/1999 | Laibowitz et al. ......... 361/321.4 |
| 5,928,609 A | * | 7/1999 | Gibson et al. .................... 422/90 |
| 5,958,787 A | | 9/1999 | Schonfeld et al. |
| 5,980,723 A | | 11/1999 | Runge-Marchese et al. |
| 6,007,775 A | | 12/1999 | Yager |
| 6,041,645 A | * | 3/2000 | Lawson et al. .................... 73/46 |
| 6,085,576 A | | 7/2000 | Sunshine et al. |
| 6,103,033 A | | 8/2000 | Say et al. |
| 6,134,461 A | | 10/2000 | Say et al. |
| 6,170,318 B1 | | 1/2001 | Lewis et al. |
| 6,200,814 B1 | | 3/2001 | Malmqvist et al. |
| 6,202,471 B1 | * | 3/2001 | Yadav et al. .................. 73/31.05 |
| 6,244,096 B1 | | 6/2001 | Lewis et al. |
| 6,290,911 B1 | | 9/2001 | Lewis et al. |
| 6,305,214 B1 | | 10/2001 | Schattke et al. |
| 6,315,956 B1 | | 11/2001 | Foulger ............................ 422/98 |
| 6,319,724 B1 | | 11/2001 | Lewis et al. |
| 6,331,244 B1 | | 12/2001 | Lewis et al. |
| 6,350,369 B1 | | 2/2002 | Lewis et al. |
| 6,387,329 B1 | | 5/2002 | Lewis et al. |
| 6,455,319 B1 | | 9/2002 | Lewis et al. |
| 6,467,333 B2 | | 10/2002 | Lewis et al. |
| 6,495,892 B2 | | 12/2002 | Goodman et al. |
| 6,537,498 B1 | | 3/2003 | Lewis et al. |
| 6,571,603 B1 | | 6/2003 | Doleman et al. |
| 6,610,367 B2 | | 8/2003 | Lewis et al. |
| 6,631,333 B1 | | 10/2003 | Lewis et al. |
| 6,752,964 B1 | | 6/2004 | Grubbs et al. |
| 6,759,010 B2 | | 7/2004 | Lewis et al. |
| 6,773,926 B1 | | 8/2004 | Freund et al. |
| 6,841,391 B2 | | 1/2005 | Lewis et al. |
| 6,844,197 B1 | | 1/2005 | Doleman et al. |
| 7,144,553 B2 | * | 12/2006 | Lewis et al. ................ 422/82.02 |
| 2001/0041366 A1 | | 11/2001 | Lewis et al. |
| 2002/0005580 A1 | | 1/2002 | Goodman et al. |
| 2002/0017125 A1 | | 2/2002 | Lewis et al. |
| 2002/0081232 A1 | | 6/2002 | Lewis et al. |
| 2002/0141901 A1 | | 10/2002 | Lewis et al. |
| 2002/0143477 A1 | | 10/2002 | Antoine et al. |
| 2002/0192117 A1 | | 12/2002 | Lewis et al. |
| 2002/0197390 A1 | | 12/2002 | Lewis et al. |
| 2003/0136960 A1 | | 7/2003 | Goodman et al. |
| 2003/0159927 A1 | | 8/2003 | Lewis et al. |
| 2004/0033165 A1 | | 2/2004 | Lewis et al. |
| 2004/0042933 A1 | | 3/2004 | Lewis et al. |
| 2004/0147038 A1 | | 7/2004 | Lewis et al. |

FOREIGN PATENT DOCUMENTS

| | | | |
|---|---|---|---|
| EP | 717418 | * | 6/1996 |
| EP | 794428 | * | 9/1997 |
| EP | 0 878 711 A1 | | 11/1998 |
| JP | 61-3039 | * | 1/1986 |
| JP | 62-257968 | * | 11/1987 |
| JP | 63-120733 | * | 5/1988 |
| JP | 63-308807 | * | 12/1988 |
| JP | 4-2958 | * | 1/1992 |
| JP | 8-264038 | * | 10/1996 |
| JP | 11-94784 | * | 4/1999 |
| WO | 86/01599 | * | 3/1986 |
| WO | WO 90/09027 | | 8/1990 |
| WO | WO 94/24561 | | 10/1994 |
| WO | 95/08113 | * | 3/1995 |
| WO | 96/07901 | * | 3/1996 |

OTHER PUBLICATIONS

W. A. Wampler et al, Chem. Mater. 1995, 7, 585-592.*
M. D. Butterworth et al, J. Colloid Interface Sci. 1995, 174, 510-517.*
G. Tourillon et al, Phys. Rev. Lett. 1986, 57, 603-606.*
J. W. Thackeray et al, J. Phys. Chem. 1986, 90, 6674-6679.*
R. E. Partch et al, ACS Symp. Ser. 1992, 492, 368-386.*
L. Moy et al, Colloq.—Inst. Natl. Rech. Agron. 1995, 75, 55-58.*
S. Breheret et al, Colloq.—Inst. Natl. Rech. Agron. 1995, 75, 103-107.*
M. Forsyth et al, Adv. Sci. Technol. 1995, 4, 279286.*
P. I. Neaves et al, Sens. Actuators B 1995, 26-27, 223-231.*
I. G. Casella et al, Anal. Chim. Acta 1996, 335, 217-225.*
F. Udrea et al, Microelectron. J. 1996, 27, 449-457.*
P. Bruschi et al, Sens. Microsyst., Proc. Ital. Conf., 1st 1996, 69-73.*
H. Yamato et al, Synth. Met. 1997, 87, 231-236.*
N. Paulsson et al, SPIE 1997, 2932, 84-90.*
V. Meister et al, Proc.—Electrochem. Soc. 1997, 97-19, 16-22.*
J. M. G. Laranjeira et al, Anal. Lett 1997, 30, 2189-2209.*
S. Baldacci et al, Sens. Mater. 1998, 10, 185-200.*
G. Banhegyi Termeszet Vilaga 1987, 118, 168-171.*
K. A. Macor et al, Inorganic Chemistry 1987, 26, 2594-2598.*
A. Fourrier-Lamer et al, Synthetic Metals 1988, 24, 95-105.*
M. Maxfield et al, J. Electrochem. Soc. 1988, 135, 299-305.*
J. R. Reynolds et al, Mat. Res. Soc. Symp. Proc. 1994, 328, 191-195.*
H. Li et al, Mat. Res. Soc. Symp. Proc. 1995, 369, 581-585.*
H.-S. Li et al, J. Electrochem. Soc. 1995, 142, 798-805.*
W. A. Wampler et al, J. Mater. Res. 1995, 10, 1811-1822.*
E. Frackowiak et al, J. Phys. Chem. Solids 1996, 57, 983-989.*
L. Toppare Turkish Journal of Chemistry 1997, 21, 30-34.*
M. De Wit et al, Synthetic Metals 1997, 85, 1303-1304.*
A. Talaie Polymer 1997, 38, 1145-1150.*
S. Sestak et al, SPIE 1997, 3241, 118-129.*
A. Galal J. Solid State Electrochem. 1998, 2, 7-15.*
L. Torsi et al, Sensors and Actuators B 1998, 48, 362-367.*
S. Kuwabata et al, J. Electrochem. Soc. 1998, 145, 2707-2710.*
Miasik, J. J. et al, Conducting Polymers, Workshop 1987, 189-198.*
Barisci, J. N. et al, Trends in Polymer Science 1996, 4, 307-311.*
Gong, K.-C. et al, Materials Research Society Symposium Proceedings 1997, 461, 87-92.*
Tan, L.-S. et al, Polymer Preprints 1997, 38, 239-240.*
Yassar, A. et al, Journal of Electroanalytical Chemistry 1988, 255, 53-69.*
Grimshaw, J. et al, Journal of Electroanalytical Chemistry 1990, 281, 125-132.*
Iyoda, T. et al, Journal of Physical Chemistry 1991, 95, 5215-5220.*
Dogan, S. et al, Synthetic Metals 1993, 60, 27-30.*
Elibol, H. et al, Journal of Macromolecular Science, Pure and Applied Chemistry 1994, A31, 593-611.*
Huang, C.-L. et al, Journal of Colloid and Interface Science 1995, 170, 275-283.*
Selampinar, F. et al, Synthetic Metals 1995, 68, 109-116.*

Hepel, M. et al, Journal of the Electrochemical Society 1996, 143, 498-505.*
Collins, G. E. et al, Synthetic Metals 1996, 78, 93-101.*
Rajeshwar, K. et al, Preprints of Papers—American Chemical Society, Division of Fuel Chemistry 1996, 41, 498-502.*
Bozkurt, A. et al, Synthetic Metals 1996, 82, 41-46.*
Talu, M. et al, Journal of Polymer Science, Part A: Polymer Chemistry 1996, 34, 2981-2989.*
Gibson, T. D. et al, Polymeric Materials Science and Engineering 1997, 76, 515-516.*
Gibson, T. D. et al, Sensors and Actuators B 1997, 44, 413-422.*
Collins, R. A. et al, Thin Solid Films 1986, 145, 133-145.*
Kurtzler, F. W. et al, Thin Solid Films 1987, 155, 1-16.*
Wilson, A. et al, Sensors and Actuators 1987, 12, 389-403.*
Haugen, G. et al, Analytical Chemistry 1988, 60, 23A-31A.*
Grate, J. W. et al, Langmuir 1988, 4, 1293-1301.*
Temofonte, T. A. et al, Journal of Applied Physics 1989, 65, 1350-1355.*
Belanger, D. et al, Analytica Chimica Acta 1990, 228, 311-315.*
Brina, R. et al, Analytical Chemistry 1990, 62, 2357-2365.*
Takada, J. et al, Applied Physics Letters 1992, 61, 2184-2186.*
Collins, G. E. et al, Journal of Vacuum Science and Technology A 1993, 11, 1383-1391.*
Charlesworth, J. M. et al, Journal of Physical Chemistry 1993, 97, 5418-5423.*
Marsella, M. J. et al, Journal of the American Chemical Society 1995, 117, 9832-9841.*
Ellis, D. L. et al, Analytical Chemistry 1996, 68, 817-822.*
Grate, J. W. et al, Chemistry of materials 1997, 9, 1201-1207.*
Dyer, D. C. et al, Sensors and Actuators A 1997, 62, 724-728.*
van Oirschot, T. G. J. et al, Technical Report No. CL-1971-17 TDCK-58753 1971, 12 pages.*
Wilson, A. et al, Physica Status Solidi A 1986, 98, 633-644.*
Santos, L. M. et al, Analytical Chemistry 1987, 59, 1766-1770.*
Sims, T. D. et al, Chemistry of Materials 1989, 1, 26-34.*
Choi, C. S. et al, Journal of the Amenrican Chemical Society 1990, 112, 1757-1768.*
Saunders, B. R. et al, Chemistry of Materials 1995, 7, 1082-1094.*
Dickinson et al., "Generating Sensor Diversity Through Combinatorial Polymer Synthesis" Anal. Cham. 1997, vol. 69, pp. 3413-3418.
Doleman et al., "Quantitative Study of the Resolving Power of Arrays of Carbon Black-Polymer Composites in Various Vapor-Sensing Tasks" Anal. Chem. 1998, 4177-4190.
Lipman, "E-noses nose out traditional odor-detection equipment" EDN magazine, Dec. 17, 1998.
Luinge et al., "Trace-level identity confirmation from infrared spectra by library searching and artificial neural networks" Analytica Chimica Acta 345 (1997) 173-184.
K. Domansky et al., "Development and Calibration of Field-Effect Transistor-Based Sensor Array for Measurement of Hydrogen and Ammonia Gas Mixtures in Humid Air", Analytical Chemistry, Feb. 1, 1998, vol. 70, No. 3, pp. 473-481.
T. C. Pearce et al., "Electronic Nose for Monitoring the Flavour of Beers", Analyst, Apr. 1993, vol. 118, pp. 371-377.
J. M. Slater et al., "Multi-layer Conducting Polymer Gas Sensor Arrays for Olfactory Sensing", Analyst, Apr. 1993, vol. 118, pp. 379-384.
M. C. Freund et al., "A chemically diverse conducting polymer-based "electronic nose"", Proceedings of the National Academy of Sciences of the United States of America, Mar. 1995, vol. 92, pp. 2652-2656.

M. C. Lonergran et al., "Array-Based Vapor Sensing Using Chemically Sensitive, Carbon Black-Polymer Resistors", Chemistry of Materials, 1996, vol. 8, No. 9, pp. 2298-2312.
Costello, et al., "Novel Composite Organic-Inorganic Semiconductor Sensors for the Quantitative Detection of Target Organic Vapours," *J. Mater. Chem.*, 6(3):289-294 (1996).
Jiakun, Wu; and Mitsutoshi Hirata; "Research into normal temperature gas-sensitive characteristics of polyaniline material" Sensors and Actuators B, 12 (1993) 11-13.
Bodenhofer et al., "Chiral Discrimination by Simple Gas Sensors," *Transducers*, 1997 International Conference on Solid-State Sensors and Actuators, Digest of Technical Papers, *Transducers* 97, Chicago, IL, Jun. 16-19, 1997, vol. 2, pp. 1391-1394, *IEEE*.
Chandiok et al., "Screening for bacterial vaginosis: a novel application of artificial nose technology," *J. Clin. Pathol.*, vol. 50, pp. 790-791 (1997).
Jiang et al., "Preparation and Properties of Organic Polymer Sub-Micrometer Function Films," *Electrets*, 1996, 9$^{th}$ International Symposium on Shanghai, China, Sep. 25-30, 1996, NY, pp. 678-683.
Lefebvre et al, "Chemical Synthesis, Characterization, and Electrochemical Studies of Poly (3,4,-ethylenedioxythiophene)/poly(styrene-4-sulfonate) composites," *Chem. Mater.*, vol. 11, No. 2, pp. 262-268 (1999).
Stussi et al., "Chemiresistive conducting polymer-based odour sensors: influence of thickness changes on their sensing properties," *Sensors and Actuators*, vol. B43, pp. 180-185 (1997).
Weherns et al., "Calibration of an array of voltammetric microelectrodes," *Analytica Chemica Acta.*, No. 334, pp. 93-101, 1996.
Williams et al., "Resolving combustible gas mixtures using gas sensitive resistors with arrays of electrodes," J. Chem. Soc., *Faraday Trans.*, vol. 92, No. 22, pp. 4497-4504, 1996.
Shurmer et al., "Integrated Arrays of Gas Sensors Using Conducting Polymers with Molecular-Sieves," *Sensors and Actuators*, vol. 4, pp. 29-33, 1991.
Cornila et al., "Capacitive sensors in CMOS technology with polymer coating," *Sensors and Actuators*, vol. 25, pp. 357-361, 1995.
Albert et al., "Cross-Reactive Chemical Sensor Arrays," *Chem. Rev.*, vol. 100, No. 7, pp. 2595-2626, 2000.
Doleman et al., "Use of compatible polymer blends to fabricate arrays of carbon black-polymer composite vapor detectors," *Anal. Chem.*, vol. 70, No. 13, pp. 2560-2564, Jul. 1, 1998.
Benes et al., "Sensors based on piezoelectric resonators," *Sensors and Actuators*, vol. A48, No. 1, pp. 1-21, 1995.
Grate et al., "Surface acoustic-wave vapor sensor based on resonator devices," *Anal. Chem.*, vol. 63, No. 17, pp. 1719-1727, Sep. 1, 1991.
Dziedzic et al, 1/f noise I polymer thick-film resistors, *J. Phys. D-Appl. Phys.*, vol. 31, pp. 2091-2097, 1998.
Fu et al., "Electrical characteristics of polymer thick film resistors, Part I: Experimental results," *IEEE Transactions on Components, Hybrids, and Manufacturing Technology*, vol. 4, No. 3, pp. 283-288, Sep. 1981.
Deen et al., "Low frequency noise in heavily doped polysilicon thin film resistors," *J. Vac. Sci. Technol.*, vol. 16, No. 4, pp. 1881-1884, Jul./Aug. 1998.
Peled et al., "1/f noise I bismuth ruthenate based thick-film resistors," *IEEE Transactions on Components, Packaging, and Manufacturing Technology*, Part A20, vol. 20, No. 3, pp. 355-360, Sep. 1997.

\* cited by examiner

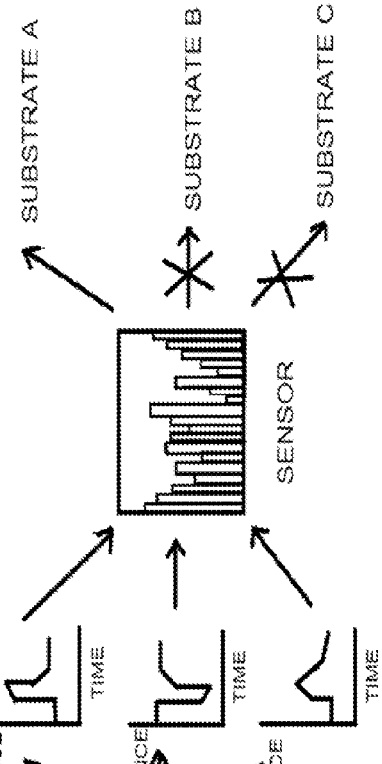
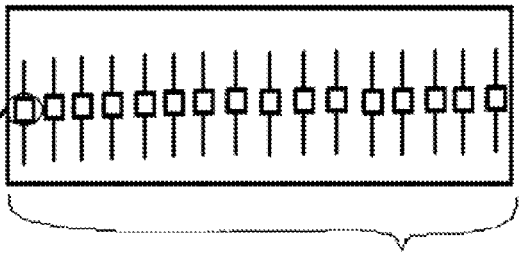
FIG. 1A-1
FIG. 1A
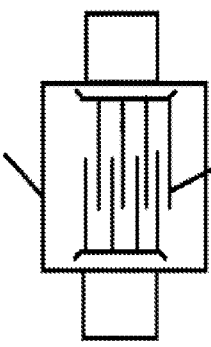
FIG. 1B

A

B

CONDUCTIVE ORGANIC SENSORS, ARRAYS AND METHODS OF USE

CROSS REFERENCE TO RELATED APPLICATIONS

This application claims priority from Provisional Application Ser. No. 60/102,817, filed Oct. 2, 1998, and Provisional Application Ser. No. 60/143,202, filed Jul. 9, 1999, to which applications a priority claim is made under 35 U.S.C. §119 (e).

The U.S. Government has certain rights in this invention pursuant to Grant Nos. DAAK-60-97-K-9503 and DAAG-55-97-1-1087 awarded by the Army Research Office.

FIELD OF THE INVENTION

This invention relates generally to sensors and sensor systems for detecting analytes in fluids and, more particularly, to sensor systems of this kind that incorporate sensors having electrical properties that vary according to the presence and concentration of analytes, and to methods of using such sensor systems.

BACKGROUND OF THE INVENTION

There is considerable interest in developing sensors that act as analogs of the mammalian olfactory system (Lundstrom et al. (1991) Nature 352:47-50; Shurmer and Gardner (1992) Sens. Act. B 8:1-11; Shurmer and Gardner (1993) Sens. Actuators B 15:32). In practice, most chemical sensors suffer from some interference by responding to chemical species that are structurally or chemically similar to the desired analyte. This interference is an inevitable consequence of the "lock" being able to fit a number of imperfect "keys". Such interferences limit the utility, of such sensors to very specific situations.

Prior attempts to produce a broadly responsive sensor array have exploited heated metal oxide thin film resistors (Gardner et al. (1991) Sens. Act. B4:117-121; Gardner et al. (1991) Sens. Act. B 6:71-75), polymer sorption layers on the surfaces of acoustic wave resonators (Grate and Abraham (1991) Sens. Act. B 3:85-111; Grate et al. (1993) Anal. Chem. 65:1868-1881), arrays of electrochemical detectors (Stetter et al. (1986) Anal. Chem. 58:860-866; Stetter et al. (1990) Sens. Act. B 1:43-47; Stetter et al. (1993) Anal. Chem. Acta 284:1-11), conductive polymers or composites that consist of regions of conductors and regions of insulating organic materials (Pearce et al. (1993) Analyst 118:371-377; Shurmer et al. (1991) Sens. Act. B 4:29-33; Doleman et al. (1998) Anal. Chem. 70:2560-2654; Lonergan et al. Chem. Mater. 1996, 8:2298). Arrays of metal oxide thin film resistors, typically based on tin oxide ($SnO_2$) films that have been coated with various catalysts, yield distinct, diagnostic responses for several vapors (Corcoran et al. (1993) Sens. Act. B 15:32-37). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal. Attempts have also been made to construct arrays of sensors with conducting organic polymer elements that have been grown electrochemically through use of nominally identical polymer films and coatings. Moreover, Pearce et al., (1993) Analyst 118:371-377, and Gardner et al., (1994) Sensors and Actuators B 18-19:240-243 describe, polypyrrole based sensor arrays for monitoring beer flavor. Shurmer (1990) U.S. Pat. No. 4,907,441, describes general sensor arrays with particular electrical circuitry. U.S. Pat. No. 4,674,320 describes a single chemoresistive sensor having a semi-conductive material selected from the group consisting of phthalocyanine, halogenated phthalocyanine and sulfonated phthalocyanine, which was used to detect a gas contaminant. Other gas sensors have been described by Dogan et al., Synth. Met. 60, 27-30 (1993) and Kukla, et al. Films. Sens. Act. B., Chemical 37, 135-140 (1996).

Sensor arrays formed from a plurality of composites that consist of regions of a conductor and regions of an insulating organic material, usually an organic polymer as described in U.S. Pat. No. 5,571,401, have some advantages relative to the approaches described above, however there is a need for sensors and sensor materials that show dramatically improved detection sensitivity if the sensors and the sensing devices are to be as sensitive as the human olfactory system towards certain classes of compounds, such as amines or thiols. The composites composed of conductors and insulating organic material have sensitivities that are primarily dictated by the swelling-induced sorption of a vapor into the composite material, and analytes that sorb to similar extents produce similar swellings and therefore produce similar detected signals (Doleman, et al., (1998) Proc. Natl. Acad. Sci. U.S.A, 95, 5442-5447). However, the human nose shows greatly enhanced sensitivity towards biogenic amines and thiols than it does towards the corresponding chain-length alcohols or alkanes, whereas this property is not displayed by composites that consist of regions of conductor and regions of a swellable insulator, whose swelling is similar for amines, thiols, alkanes, alcohols, and other materials of similar vapor pressure to each other. Certain odors have typically been missed by an electronic nose that is not responsive to such odors at least at the level comparable to a human, and such a device will not be acceptable to detect and classify odors that are perceived by humans or at levels that are desirable for food freshness, biomedical, disease state identification, and other applications.

Breath testing has long been recognized as a nonintrusive medical technique that allows for diagnosis of disease or the presence of analytes. Presently, the techniques utilized for the evaluation of breath are gas chromatography with flame photometric detection (FPD), GC/MS (mass spectrometry), the Halimeter, microbiological testing, and organoleptic scores (Spielman, 1998). Both GC/FPD and GC/MS are quantitative techniques, with GC/MS having the added advantage of identifying the individual components of analyzed breath. However, both of these instruments are costly and time intensive, which limits their use in common practice. The Halimeter is a portable, electrochemically-based sulfide monitor introduced within the last decade to monitor for halitosis by measuring the concentration of sulfur containing compounds semiquantitatively at the part per billion level. However, one drawback is that the Halimeter is unable to detect individual sulfur compounds, because it is comprised of a single sensor that responds to the general class of sulfur containing compounds, such as hydrogen sulfide and methylmercaptan. Furthermore, it is unable to detect many other objectionable odoriferous compounds such as indole, skatole, volatile fatty acids, and amines, which are present in breath of halitosis patients. Additionally, the halimeter sensor is not entirely selective because it also responds to alcohols such as ethanol. In addition, it can not detect the presence of volatile amines or other compounds that are of interest in disease other than certain types of halitosis. Odor panels have been utilized efficiently in some cases for the analysis of disease. Some of the drawbacks are of course that odor panels consist of humans that are genetically capable and highly trained, and that the scores are subjective.

Although the foregoing systems have some usefulness, there still remains a need in the art for a low cost, broadly responsive analyte detection sensor array based on a variety of sensors.

SUMMARY OF THE INVENTION

The present artificial olfactory system (or electronic nose) uses an array of many different receptors to recognize a single odorant. In such a configuration, the burden of recognition is not on highly specific receptors, as in the traditional "lock-and-key" molecular recognition approach to chemical sensing, but lies instead on the distributed pattern processing of the olfactory bulb and the brain.

The present invention fulfills this and other needs. It is therefore an object of the invention to provide a broadly responsive analyte detection sensor array based on a variety of "chemiresistor" elements. Such elements are simply prepared and are readily modified chemically to respond to a broad range of analytes. In addition, these sensors yield a rapid, low-power, dc electrical signal in response to the analyte of interest, and their signals are readily integrated with software- or hardware-based algorithms including neural networks for purposes of analyte identification.

In addition, a second object of the present invention is to provide individual sensor materials that display enhanced sensitivity towards certain specific compounds of interest, such as, for example, biogenic amines, thiols, and other similar compounds. The sensor comprises regions of an electrically-conductive organic material and regions of a conductive material compositionally different than said organic material, wherein the sensor provides an electrical path through the regions of the organic material and the conductive material, the sensors constructed to provide a first response when contacted with a first chemical analyte and a second different response when contacted with a second different chemical analyte. In one embodiment, the conductive organic material is selected from the group consisting of polyanilines, polypyrroles, polythiophenes, poly EDOTs and derivatives thereof, and the conductive material is selected from the group consisting of Ag, Au, Cu, Pt, AuCu, and carbon black. These sensors can be used, by themselves or in conjunction with other sensor modalities (surface acoustic wave device, electrochemical gas sensors, etc.) to increase the performance and information content of sensor arrays for detection of analytes in a sample.

In another embodiment, the present invention provides a sensor array comprising a plurality of sensors and a measuring apparatus, wherein the sensor are in communication with the measuring apparatus, at least one of the sensors comprising regions of an electrically conducting organic material and regions of a conductive material compositionally different than said organic material, wherein said sensor provides an electrical path through the regions of the organic material and the conductive material, the sensors constructed to provide a first response when contacted with a first chemical analyte and a second, different response when contacted with a second different chemical analyte. In one embodiment, the sensors in the array are comprised of compositionally different combinations of materials having regions of an organic conductive material and regions of a compositionally dissimilar electrical conductor, wherein the conductive organic material is selected from the group consisting of polyanilines, polypyrroles, polythiophenes, polyEDOTs, and derivatives thereof, and the compositionally different conductive material is selected from the group consisting of Ag, Au, Cu, Pt, carbon black and AuCu. In another embodiment, at least one of the sensors in the array consists of a material comprised of regions of an electrically-conductive organic material and regions of a conductive material compositionally different than said organic material, wherein the sensor provides an electrical path through the regions of the organic conducting material and the compositionally dissimilar conductive material.

In another embodiment, the present invention provides a sensor array system comprising a plurality of sensors and a measuring apparatus, wherein the sensors are in communication with the measuring apparatus, and a computer comprising a resident algorithm, at least one of the sensors comprising regions of an electrically conductive organic material and regions of a conductive material compositionally different than the organic material, wherein said sensor provides an electrical path through the regions of the organic material and the regions of the conductive material, the sensors constructed to provide a first response when contacted with a first chemical analyte, and a second response when contacted with a second chemical analyte, wherein the computer processes the difference between the first response and the second response. The measuring apparatus can be, for example, an electrical measuring device in electrical communication with at least one sensor. The sensor array system may further include a temperature control apparatus, the temperature control apparatus being in thermal communication with at least one sensor.

In yet another embodiment, the present invention provides a method for detecting the presence of an analyte in a sample, the method comprising sensing the presence of an analyte in a sample with a sensor array comprising a plurality of chemically sensitive resistors, at least one of which comprises regions of an electrically conductive organic material and regions of a conductive material compositionally different than said organic material, said resistor providing an electrical path through the regions of organic material and the regions of the conductive material, and providing a first electrical resistance when contacted with a first sample comprising a first chemical analyte and a second different electrical resistance when contacted with a second sample comprising a second chemical analyte.

In another embodiment, the present invention provides a method for detecting a microorganism, the method comprising exposing an analyte associated with the microorganism to a sensor array comprising a plurality of sensors electrically connected to measuring apparatus, wherein at least one of the sensors comprises regions of an electrically conductive organic material and regions of a conducting material compositionally different than said organic material; and measuring a response of the sensors, thereby detecting the microorganism.

In yet another embodiment a system for identifying a microorganism is provided. The system includes a sensor array comprising a plurality of sensors connected to a measuring apparatus, wherein at least one of the sensors comprises regions of an electrically conductive organic material and regions of a conducting material compositionally different than said organic material; and a computer comprising a resident algorithm; the measuring apparatus capable of detecting a response from the each sensor and the computer capable of assembling the responses into a response profile for microorganism identification. The resident algorithm is selected from the group consisting of principal component analysis, Fisher linear analysis, neural networks, genetic algorithms, fuzzy logic, pattern recognition, and combinations thereof.

In yet another embodiment, a system for detecting an analyte in a sample to be tested is provided. The system includes a substrate having a sensor that incorporates at least one sensor comprising an electrically conductive organic material and a compositionally different conductive material and that provides a response that varies according to the presence of an analyte in contact with it; a detector operatively associated with the sensor, for measuring the response of the sensor; a sample delivery unit for delivering the sample to be tested to the sensor; and an information storage and processing device configured to store an ideal response for a predetermined analyte and to compare the response of the sensor with the stored ideal response, to detect the presence of the analyte in the sample being tested. Where the sample to be tested is a liquid, the sample delivery unit comprises a flow passage interconnecting the sensor with a region containing the liquid to be tested, a gas-permeable, liquid-impermeable shield interposed in the flow passage, and a device for extracting vapor from the liquid to be tested and for delivering the extracted vapor along the flow passage to the sensor. Where the sample is gaseous the sample delivery unit comprises a wand or other means of defining a gas flow passage, and a fan or pump for transporting the gaseous sample to the sensor. The detector or measuring device is optimized to detect a member selected from the group consisting of electromagnetic energy, optical properties, resistance, capacitance, inductance, impedance and combinations thereof.

In yet another embodiment, the present invention provides a method for detecting a disease in a subject, the method comprising, contacting an array of sensors with a biological sample suspected of containing an analyte indicative of the disease, wherein at least one of the sensors comprises regions of an electrically conductive organic material and regions of a conductive material compositionally different than said organic material; and detecting the analyte wherein the presence of the analyte is indicative of the disease. The disease can be any disease such as, for example a disease selected from the group consisting of halitosis, periodontal disease, pneumonia, vaginitis, uremia, trimethylaminuria, lung cancer, dysgensia, dysosnia, cytinuria, and bacterial vaginosis. The analyte can be an off gas of a member selected from the group consisting of *Prevotella intermedia, Fusobacterium nucleatum, Porphyromonas gingivalis, Porphyromonas endodontalis, Prevotella loescheii, Hemophilus parainfluenzae, Stomatococcus muci, Treponema denticola, Veillonella species, Peptostreptococcus anaerobius, Micros prevotii, Eubacterium limosum, Centipeda periodontii, Selemonad aremidis, Eubacterium species, Bacteriodes species, Fusobacterium periodonticum, Prevotella melaminogenica, Klebsiella pneumoniae, Enterobacter cloacae, Citrobacter species* and *Stomatococcus mucilaginus*. The biological sample includes for example, a subject's breath, vaginal discharge, urine, feces, tissue sample, or blood sample.

BRIEF DESCRIPTION OF THE FIGURES

These and other objects of the present invention will now be described in detail with reference to the accompanying drawing, in which.

DETAILED DESCRIPTION OF THE INVENTION

Figure 1C:
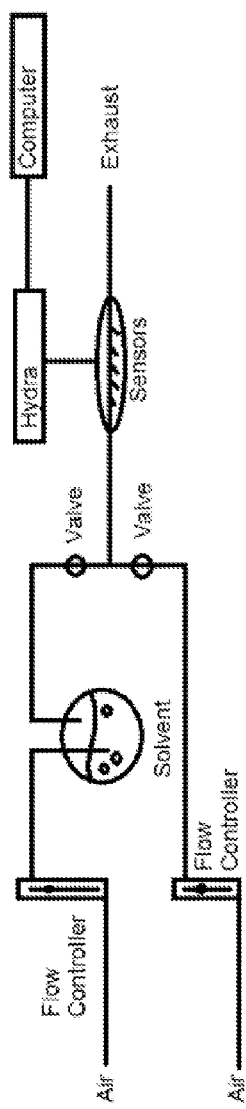
FIG. 1A shows an overview of sensor design; 1B, shows an overview of sensor operation; and 1C, shows an overview of system operation.

The sensors and sensor arrays disclosed herein act as an "electronic nose" to offer ease of use, speed, and identification of analytes and/or analyte regions all in a portable, relatively inexpensive implementation. Thus, a wide variety of analytes and fluids may be analyzed by the disclosed sensors, arrays and noses so long as the subject analyte is capable generating a differential response across a plurality of sensors of the array. Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, and the like. A wide variety of commercial applications are available for the sensors arrays and electronic noses including, but not limited to, environmental toxicology and remediation, biomedicine, materials quality control, food and agricultural products monitoring, heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery and telesurgery. Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anaesthetics.

Biogenic amines such as putrescine, cadaverine, and spermine are formed and degraded as a result of normal metabolic activity in plants, animals and microorganisms, and have been identified and quantified using analytical techniques such as gas chromatography-mass spectrometry (GC-MS), high performance liquid chromatography (HPLC) or array based vapor sensing in order to assess the freshness of foodstuffs such as meats (Veciananogues, 1997, J. Agr. Food Chem., 45:2036-2041), cheeses, alcoholic beverages, and other fermented foods. Additionally, aniline and o-toluidine have been reported to be biomarkers for patients having lung cancer (Preti et al., 1988, J. Chromat. Biomed. Appl. 432:1-11), while dimethylamine and trimethylamine have been reported to be the cause of the "fishy" uremic breath odor experienced by patients with renal failure. (Simenhoff, 1977, New England J. Med., 297:132-135) Thus, in general biogenic amines and thiols are biomarkers of bacteria, disease states, food freshness, and other odor-based conditions. Thus, the electronic nose sensor elements and arrays discussed herein incorporating these materials can be used to monitor the components in the headspace of urine, blood, sweat, and saliva of human patients, as well as breath, to diagnose various states of health and disease. In addition, they can be used for food quality monitoring, such as fish freshness (which involves volatile amine signatures), for environmental and industrial applications (oil quality, water quality, air quality and contamination and leak detection), for other biomedical applications, for law enforcement applications (breathalayzers), for confined space monitoring (indoor air quality, filter breakthrough, etc) and for other applications delineated above to add functionality and performance in an unanticipated fashion to existing sensor arrays though improvement in their properties by use in arrays that combine sensor modalities. For example, surface acoustic wave (SAW) arrays, quartz crystal microbalance arrays, composites consisting of regions of conductors and regions of insulators, bulk semiconducting organic polymers, and other array types exhibit improved performance towards vapor discrimination and quantification when the sensors of the present invention are incorporated additionally into arrays that contain these other sensing modalities (e.g., wherein the array of sensors comprises a member selected from the group consisting of a metal oxide gas sensor, a conducting polymer sensor, a dye-impregnated polymer film on fiber optic detector, a polymer-coated micromirror, an electrochemical gas detector, a chemically sensitive field-effect transistor, a carbon black-polymer composite, a micro-electro-mechanical system device and a micro-opto-electro-mechanical system device).

Breath testing has long been recognized as a nonintrusive medical technique that might allow for the diagnosis of disease by linking specific volatile organic vapor metabolites in exhaled breath to medical conditions (see Table 1). In addition to breath analysis being nonintrusive, it offers several other potential advantages in certain instances, such as 1) breath samples are easy to obtain, 2) breath is in general a much less complicated mixture of components than either serum or urine samples, 3) direct information can be obtained on the respiratory function that is not readily obtainable by other means, and 4) breath analysis offers the potential for direct real time monitoring of the decay of toxic volatile substances in the body. Table 1 lists some of the volatile organic compounds that have been identified as targets for specific diseases using gas chromatography/mass spectrometry (GC/MS) methods, with emphasis on amines.

TABLE 1

| Patient Diagnosis | Target VOCs | VOC Source |
|---|---|---|
| Uremia; Preti, 1992; Simenhoff, 1977; Davies, 1997 | dimethylamine, trimethylamine | breath, urine |
| Trimethylaminuria; Preti, 1992; Alwaiz, 1989 | trimethylamine | breath, urine, swat, vaginal discharge |
| Lung Cancer; Preti, 1992 | aniline, o-toluidine | lung air |
| Dysgeusia/Dysosmia; Preti, 1992; Oneill, 1988 | hydrogen sulfide, methyl mercaptn, pyridine, aniline, diphenylamine, dodecanol | lung air |
| Cystinuria; Manolis A., 1983, Clin. Chem. 29:5. | cadaverie, piperidine, putrescine, pyrrolidine | breath |
| Halitosis; Kozlovsky, 1994; Preti, 1992 | hydrogen sulfide, methyl mercaptan, cadaverine, putrescine, indole, skatole | mouth air |
| Bacterial Vaginosis; Chandiok, 1997, J. Clinical Path., 50:790. | amines | vaginal cavity and discharge | differing conductivity transverse to the electrical path between the conductive leads. Generally, at least one of the sensors is fabricated by blending a conductive material with a conductive organic material. For example, in a colloid, suspension or dispersion of particulate conductive material in a region of conductive organic material, the regions separating the particles provide changes in conductance relative to the conductance of the particles themselves. The gaps of different conductance arising from the organic conductive material range in path length from about 10 to 1,000 angstroms, usually on the order of 100 angstroms. The path length and resistance of a given gap is not constant but rather is believed to change as the material absorbs, adsorbs or imbibes an analyte. Accordingly the dynamic aggregate resistance provided by these gaps in a given resistor is a function of analyte permeation of the conductive organic regions of the material. In some embodiments, the conductive material may also contribute to the dynamic aggregate resistance as a function of analyte permeation (e.g., when the conductive material is a conductive organic polymer such as polypyrrole and is blended with another organic conducting material to form the composite).

A wide variety of conductive materials and dissimilar conductive organic materials can be used. In one embodiment, one such region is comprised of an inorganic (Au, Ag) or organic (carbon black) conductive material, while the other region is comprised of a compositionally dissimilar organic conducting polymer (polyaniline, polypyrrole, polythiophene, polyEDOT, and other conducting organic polymers such as those in the Handbook of Conducting Polymers (Handbook of Conducting Polymers, second ed., Marcel Dekker, New York 1997, vols. 1 & 2)). Other combinations of conductor/organic conductor/composite materials are also useful.

In one implementation, an electrically conductive organic material that is dopable or undopable by protons (Scheme 1) can be used as the organic material in a composite where the compositionally different conductor is carbon black:

Scheme 1:

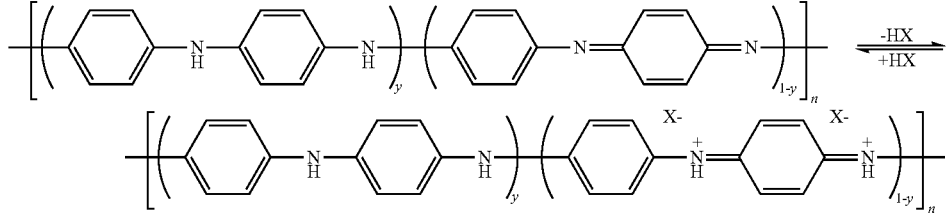

With reference now to the drawings, and particularly to FIG. 1, there is shown a sensor array for detecting an analyte in a fluid for use in conjunction with an electrical measuring apparatus. The array comprises a plurality of differently responding chemical sensors, at least one of the sensors comprising at least first and second conductive leads electrically coupled to and separated by a chemically sensitive resistor. The leads may be any convenient conductive material, usually a metal, and may be interdigitized to maximize signal-to-noise strength (see FIG. 1A).

At least one sensor in the array is composed of a material comprising regions of an organic electrical conductor with regions of a compositionally dissimilar material that is an electrical conductor. The resistor comprises a plurality of alternating regions of differing compositions and therefore Polyaniline is a desirable member in the class of conducting polymers in that the half oxidized form, the emeraldine base (y=0.5), is rendered electrically conductive upon incorporation of a strong acid. The conductive form of polyaniline, commonly referred to as the emeraldine salt (ES), has been reported to deprotonate to the emeraldine base and become insulating in alkaline environments. Without being bound to any particular theory, the polyaniline may also undergo a beneficial phase transition that also contributes to the superior performance of such composites.

Table 2 provides exemplary conductive materials for use in sensor fabrication; blends, such as of those listed, may also be used. Typically conductors include, for example, those having a positive temperature coefficient of resistance. The sensors are comprised of a plurality of alternating regions of a conductor with regions of a compositionally dissimilar conducting organic material. Without being bound to any particular theory, it is believed that the electrical pathway that an electrical charge traverses between the two contacting electrodes traverses both
the regions of the conductor and the regions of the organic material.

TABLE 2

| Major Class | Examples |
| --- | --- |
| Organic Conductors | conducting polymers (poly(anilines), poly(thiophenes), poly(pyrroles), poly(aceylenes, etc.)), carbonaceous material (carbon blacks, graphite, coke, C60 etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, MoS2, TiO2, etc.), conductive metal oxides (In2O3, SnO2, Na2Pt3O4, etc.), superconductors (Yba2Cu3O7, Ti2Ba2Ca2Cu3O10, etc.), etc. |
| Mixed inorganic/ organic Conductor | Tetracyanoplatinate complexes, Iridium halocarbonyl complexes, stacked macrocyclic complexes. Etc. |

In this embodiment, the conducting region can be anything that can carry electrons from atom to atom, including, but not limited to, a material, a particle, a metal, a polymer, a substrate, an ion, an alloy, an organic material, (e.g., carbon, graphite, etc.) an inorganic material, a biomaterial, a solid, a liquid, a gas or regions thereof.

In certain other embodiments, the conductive material is a conductive particle, such as a colloidal nanoparticle. As used herein the term "nanoparticle" refers to a conductive cluster, such as a metal cluster, having a diameter on the nanometer scale. Such nanoparticles are optionally stabilized with organic ligands.

Examples of colloidal nanoparticles for use in accordance with the present invention are described in the literature. In this embodiment, the electrically conductive organic region, can optionally be a ligand that is attached to a central core making up the nanoparticle. These ligands i.e., caps, can be polyhomo- or polyhetero-functionalized, thereby being suitable for detecting a variety of chemical analytes. The nanoparticles, i.e., clusters, are stabilized by the attached ligands. In certain embodiments, the conducting component of the resistors are nanoparticles comprising a central core conducting element and an attached ligand optionally in a polymer matrix. With reference to Table 2, various conducting materials are suitable for the central core. In certain preferred embodiments, the nanoparticles have a metal core. Preferred metal cores include, but are not limited to, Au, Ag, Pt, Pd, Cu, Ni, AuCu and regions thereof. Gold (Au) is especially preferred. These metallic nanoparticles can be synthesized using a variety of methods. In a preferred method of synthesis, a modification of the protocol developed by Brust et al. can be used. (see, Brust, M.; Walker, M.; Bethell, D.; Schiffrin, D. J.; Whyman, R. J. Chem. Soc., Chem. Commun., 1994, 801-802.) As explained more fully below, by varying the concentration of the synthetic reagents, the particle size can be manipulated and controlled.

Table 3 provides exemplary electrically conductive organic materials that can be used to form the organic conducting regions of the sensors.

TABLE 3

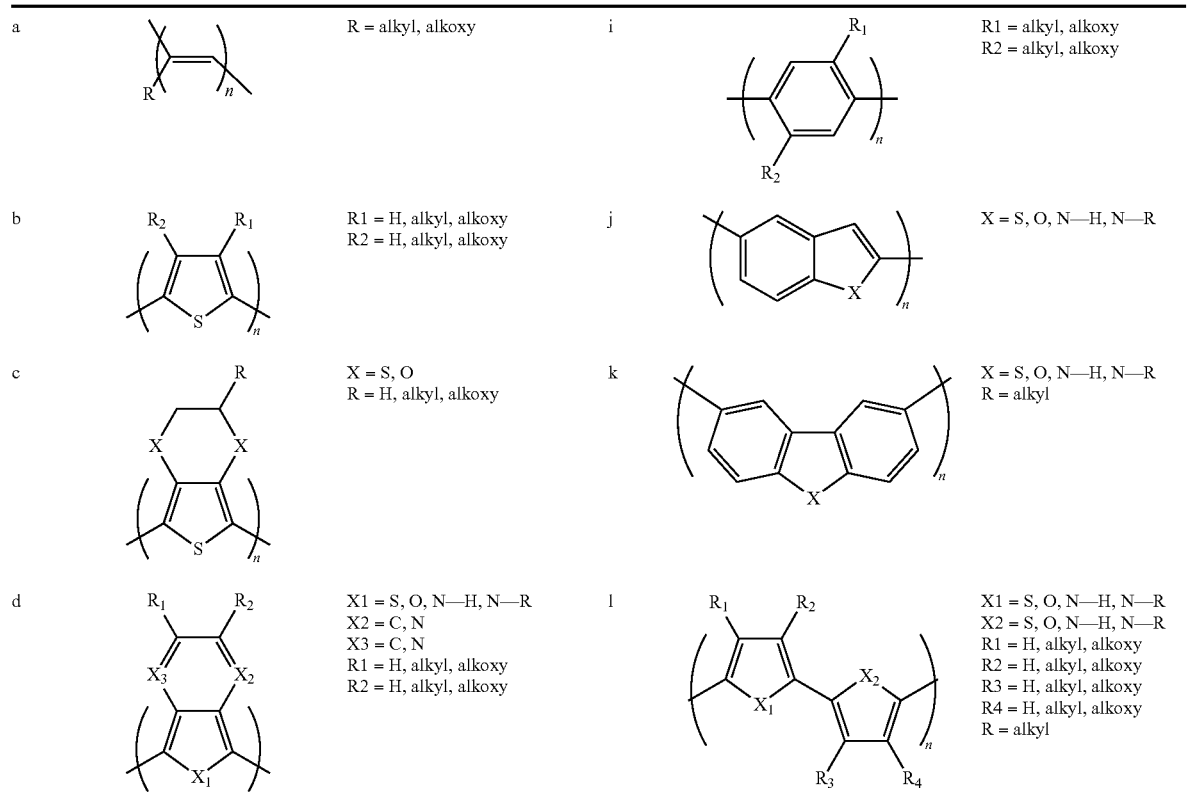

TABLE 3-continued
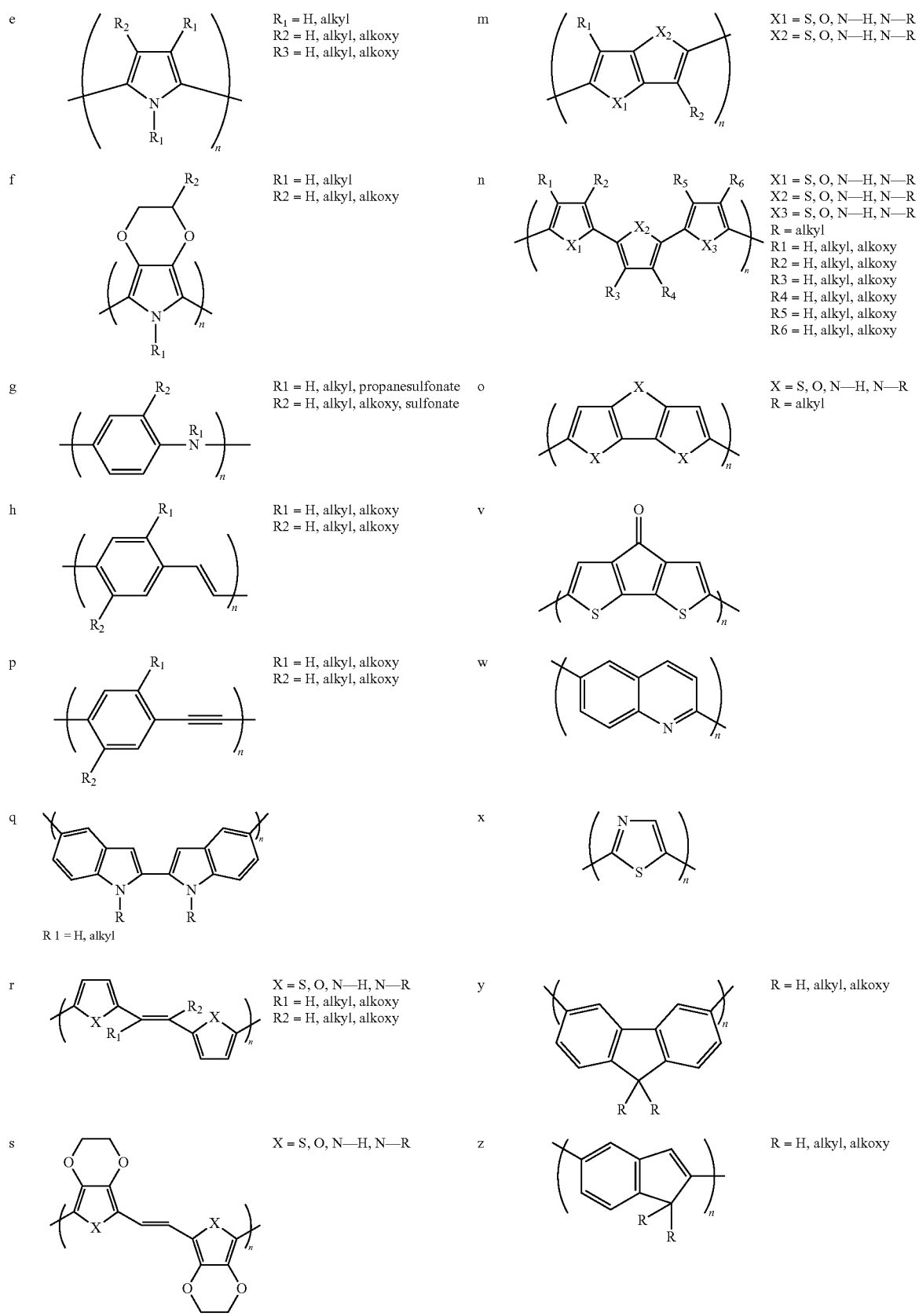

TABLE 3-continued

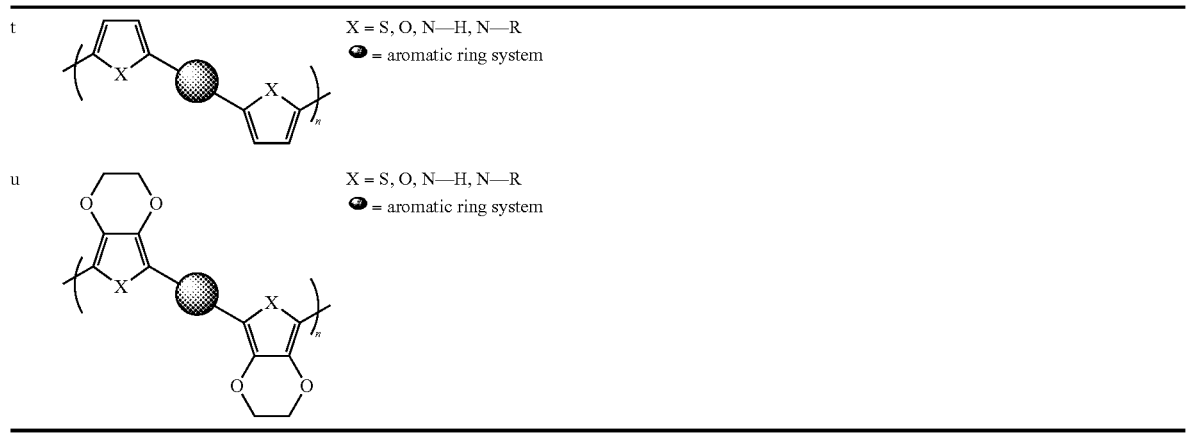

a. Poly(acetylene) and derivatives
b. Poly(thiophenes) and derivatives
c. Poly(3,4-ethylenedioxythiophene) and poly(3,4-ethylenedithiathiophene) and derivatives
d. Poly(isathianaphthene), poly(pyridothiophene), poly(pyrizinothiophene), and derivatives
e. Poly(pyrrole) and derivatives
f. Poly(3,4-ethylenedioxypyrrole) and derivatives
g. Poly(aniline) and derivatives
h. Poly(phenylenevinylene) and derivatives
I. Poly(p-phenylene) and derivatives
j. Poly(thianapthene), poly(benxofuran), and poly(indole) and derivatives
k Poly(dibenzothiophene), poly(dibenxofuran), and poly(carbazole) and derivatives
l. Poly(bithiophene), poly(bifuran), poly(bipyrrole), and derivatives
m. Poly(thienothiophene), poly(thienofuran), poly(thienopyrrole), poly(furanylpyrrole), poly(furanylfuran), poly(pyrolylpyrrole), and derivatives
n. Poly(terthiophene), poly(terfuran), poly(terpyrrole), and derivatives
o. Poly(dithienothiophene), poly(difuranylthiophene), poly(dipyrrolylthiophene), poly(dithienofuran), poly(dipyrrolylfuran), poly(dipyrrolylpyrrole) and derivatives
p. Poly(phenyl acetylene) and derivatives
q. Poly(biindole) and derivatives
r. Poly(dithienovinylene), poly(difuranylvinylene), poly(dipyrrolylvinylene) and derivatives
s. Poly(1,2-trans(3,4-ethylenedioxythienyl)vinylene), poly(1,2-trans(3,4-ethylenedioxyfuranyl)vinylene), and poly(1,2-trans(3,4-ethylenedioxypyrrolyl)vinylene), and derivatives
t. The class of poly(bis-thienylarylenes) and poly(bis-pyrrolylarylenes) and derivatives
u. The class of poly(bis(3,4-ethylenedioxythienyl)arylenes) and derivatives
v. Poly(dithienylcyclopentenone)
w. Poly(quinoline)
x. Poly(thiazole)
y. Poly(fluorene) and derivatives
z. Poly(azulene) and derivatives
Notes:
a. Aromatics = phenyl, biphenyl, terphenyl, carbazole, furan, thiophene, pyrrole, fluorene, thiazole, pyridine, 2,3,5,6-hexafluorobenzene, anthracene, coronene, indole, biindole, 3,4-ethylenedioxythiophene, 3,4-ethylenedioxypyrrole, and both the alkyl and alkoxy derivatives of these aromatics.
b. Alkyl = aliphatic group branched or straight chain ranging from $CH_3$ to $C_{20}H_{41}$.
c. Alkoxy = OR, where R is an aliphatic group that may either be branched or straight chain ranging from $CH_3$ to $C_{20}H_{41}$.
d. All conductive polymers are depicted in their neutral, nonconductive form. The polymers listed in the figure are doped oxidatively either by means chemically or electrochemically.
e. The class of polyanilines are acid doped and can be done so with a number of sulfonic acids including methane sulfonic acid, ethane sulfonic acid, propane sulfonic acid, butane sulfonic acid, pentane sulfonic acid, hexane sulfonic acid, heptane sulfonic acid, octane sulfonic acid, nonane sulfonic acid, decane sulfonic acid, ondecane sulfonic acid, dodecane sulfonic acid, dodecylbenzenesulfonic acid, toluene sulfonic acid, benzene sulfonic acid, dinonanylnaphthalene sulfonic acid, and both the d and l forms of camphor sulfonic acid.
f. All other class of conductive polymers when doped there is an associated counter ion to compensate the positive charges on the backbone. These can be perchlorate, hexafluorophosphate, tetrafluoroborate, fluoride, chloride, bromide, iodide, triflate, etc.

The conductive organic material can be either an organic semiconductor or organic conductor. "Semi-conductors" as used herein, include materials whose electrical conductivity increases as the temperature increases, whereas conductors are materials whose electrical conductivity decreases as the temperature increases. By this fundamental definition, the organic materials that are useful in the sensors of the present invention are either semiconductors or conductors. Such materials are collectively referred to herein as electrically conducting organic materials because they produce a readily-measured resistance between two conducting leads separated by about 10 micron or more using readily-purchased multi-meters having resistance measurement limits of 100 Mohm or less, and thus allow the passage of electrical current through them when used as elements in an electronic circuit at room temperature. Semi-conductors and conductors can be differentiated from insulators by their different room temperature electrical conductivity values. Insulator show very low room temperature conductivity values, typically less than about $10^{-8}$ $ohm^{-1}$ $cm^{-1}$. Poly(styrene), poly(ethylene), and other polymers elaborated in Table 4 provide examples of insulating organic materials. Metals have very high room temperature conductivities, typically greater than about 10 $ohm^{-1}$ $cm^{-1}$. Semi-conductors have conductivities greater than those of insulators, and are distinguished from metals by their different temperature dependence of conductivity, as described above. Examples of semiconducting and conducting organic material are provided in Table 3. The organic materials that are useful in the sensors of the present invention are either electrical semiconductors or conductors, and have room temperature electrical conductivities of greater than about $10^{-6}$ $ohm^{-1}$ $cm^{-1}$, preferably having a conductivity of greater than about $10^{-3}$ $ohm^{-1}$ $cm^{-1}$.

Accordingly, the sensors of the present invention include sensors comprising regions of an electrical conductor and regions of a compositionally different organic material that is an electrical conductor or semiconductor. As used above, electrical conductors include, for example, Au, Ag, Pt and carbon black, other conductive materials having similar resistivity profiles are easily identified in the art (see, for example the latest edition of: *The CRC Handbook of Chemistry and Physics*, CRC Press, the disclosure of which is incorporated herein by reference).

Furthermore, insulators can also be incorporated into the composite to further manipulate the analyte response properties of the composites. The insulating region (i.e., non-conductive region) can be anything that can impede electron flow from atom to atom, including, but not limited to, a material, a polymer, a plasticizer, an organic material, an organic polymer, a filler, a ligand, an inorganic material, a biomaterial, a solid, a liquid, a gas and regions thereof. Table 4 provides examples of insulating organic materials that can be used for such purposes.

TABLE 4

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), etc. |
| Main-chain acyclic heteroatom polymers | poly(oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), etc. |
| Main-chain heterocyclic polymers | poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), poly(diabenzofurans), poly(phthalides), poly(acetals), poly(anhydrides), carbohydrates, etc. |

Nonconductive organic polymer materials; blends and copolymers; plasticized polymers; and other variations including those using the polymers listed here, may also be used. Combinations, concentrations, blend stoichiometries, percolation thresholds, etc. are readily determined empirically by fabricating and screening prototype resistors (chemiresistors) as described below.

The chemiresistors can be fabricated by many techniques such as, but not limited to, solution casting, suspension casting, and mechanical mixing. In general, solution cast routes are advantageous because they provide homogeneous structures and ease of processing. With solution cast routes, sensor elements may be easily fabricated by spin, spray or dip coating. Since all elements of the sensor film must be soluble, however, solution cast routes are somewhat limited in their applicability. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting, compositionally dissimilar organic conducting and non-conducting material or their reaction precursors are soluble in a common solvent, the chemiresistors can be fabricated by solution casting. The oxidation of pyrrole by phosphomolybdic acid represents such a system. In this reaction, the phosphomolybdic acid and pyrrole are dissolved in tetrahydrofuran (THF) and polymerization occurs upon solvent evaporation. This allows for THF soluble compositionally different conductive, semiconductive, and non-conductive materials to be dissolved into this reaction region thereby allowing the composite to be formed in a single step upon solvent evaporation. The choice of compositionally different conductive or conductive organic materials in this route is, of course, limited to those that are soluble in the reaction media.

A variety of permutations on this scheme are possible for other conducting polymers. Some of these are listed below. Certain conducting organic polymers, such as substituted poly-(cyclooctatetraenes), are soluble in their undoped, non-conducting state in solvents such as THF or acetonitrile. Consequently, the blends between the undoped polymer and other organic materials can be formed from solution casting. After which, the doping procedure (exposure to $I_2$ vapor, for instance) can be performed on the blend to render the substituted poly(cyclooctatetraene) conductive. Again, the choice of compositionally different organic materials is limited to those that are soluble in the solvents that the undoped conducting polymer is soluble in and to those stable to the doping reaction.

Certain conducting organic polymers can also be synthesized via a soluble precursor polymer. In these cases, blends between the precursor polymer and the compositionally different material of the composite can first be formed followed by chemical reaction to convert the precursor polymer into the desired conducting polymer. For instance poly(p-phenylene vinylene) can be synthesized through a soluble sulfonium precursor. Blends between this sulfonium precursor and a non-conductive or conductive polymer can be formed by solution casting. After which, the blend can be subjected to thermal treatment under vacuum to convert the sulfonium precursor to the desired poly(p-phenylene vinylene).

In suspension casting, one or more of the components of the sensor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the conductive organic or conductive polymer is dissolved in an appropriate solvent (such as THF, acetonitrile, water, etc.). Carbon black is then suspended in this solution and the resulting region is used to dip coat or spray coat electrodes.

Mechanical mixing is suitable for all of the conductive/conductive organic/non-conductive combinations possible. In this technique, the materials are physically mixed in a ball-mill or other mixing device. For instance, carbon black/conducting organic polymer composites are readily made by ball-milling. When the semiconductive or conductive organic material can be melted or significantly softened without decomposition, mechanical mixing at elevated temperature can improve the mixing process. Alternatively, composite fabrication can sometimes be improved by several sequential heat and mix steps.

Once fabricated, the individual sensors can be optimized for a particular application by varying their chemical make up and morphologies. The chemical nature of the sensors determines to which analytes they will respond and their ability to distinguish different analytes. The relative ratio of conductive to compositionally different organic conductive or semiconductive organic material, along with the composition of any other insulating organic or inorganic components, can determine the magnitude of the response since the resistance of the elements becomes more sensitive to sorbed molecules as the percolation threshold is approached and as the molecules interact chemically with the components of the composite that adsorb or absorb the analyte. The film morphology is also important in determining response characteristics. For instance, uniform thin films respond more quickly to analytes than do uniform thick ones. Hence, with an empirical catalogue of information on chemically diverse sensors made with varying ratios of semiconductive, conducting, and insulating components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high melting temperature (Tm) polymers), the incorporation of the resistor elements into supporting matrices such as clays or polymer networks (forming the resistor blends within poly-(methylmethacrylate) networks or within the lamellae of montmorillonite, for instance), etc. In another embodiment, the resistor is deposited as a surface layer on a solid matrix which provides means for supporting the leads. Typically, the matrix is a chemically inert, non-conductive substrate such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analog signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different organic materials and conducting components suspended or dissolved in solution which can be deposited are used. A sensor array of a million distinct elements only requires a 1 cm×1 cm sized chip employing lithography at the 10 micrometer feature level, which is within the capacity of conventional commercial processing and deposition methods. This technology permits the production of sensitive, small-sized, stand-alone chemical sensors.

In one embodiment, the sensor arrays have a predetermined inter-sensor variation in the structure or composition of the conductive or semiconductive organic materials as well as in the conductive components and any insulating or plastizing components of the composites. The variation may be quantitative and/or qualitative. For example, the concentration of the conductive or semiconductive organic material in the composite can be varied across sensors. Alternatively, a variety of different organic materials may be used in different sensors. The anions that accompany conducting or semiconducting organic polymers such as polyaniline in some doping states can be compositionally varied to add diversity to the array, as can the polymer composition itself, either structurally (through use of a different family of materials) or through modification of the backbone and/or side chains of the basic polymer structure. This ability to fabricate many chemically different materials allows ready incorporation of a wide range of chemical diversity into the sensor elements, and also allows facile control over the electrical properties of the sensor elements through control over the composition of an individual sensor element in the array. Insulating organic materials can also be used and blended into the array in order to further increase the diversity in one embodiment of the invention. When insulators are added, commercial, off-the-shelf, organic polymers can provide the basic sensor components that respond differently to different analytes, based on the differences in polarity, molecular size, and other properties of the analyte in order to achieve the chemical diversity amongst array elements in the electronic nose sensors. Such insulators would include main-chain carbon polymers, main chain acyclic heteroatom polymers, main-chain heterocyclic polymers, and other insulating organic materials. Otherwise, these properties can be obtained by modification in the composition of the electrically conductive or electrically semiconductive organic component of the sensor composition by use of capping agents on a colloidal metal part of the conductive phase, by use of different plasticizers added to otherwise compositionally identical sensor elements to manipulate their analyte sorption and response properties, by variation in the temperature or measurement frequency of the sensors in an array of sensors that are otherwise compositionally identical, or a combination thereof and with sensors that are compositionally different as well. The sensors in an array can readily be made by combinatorial methods in which a limited number of feedstocks is combined to produce a large number of chemically distinct sensor elements.

One method of enhancing the diversity of polymer based conductor/conductor or conductor/semiconductor chemiresistors is through the use of polymer blends or copolymers (Doleman, et al. (1998) Anal. Chem. 70, 2560-2654). Immiscible polymer blends may also be of interest because carbon black or other conductors can be observed to preferentially segregate into one of the blend components. Such a distribution of carbon black conduction pathways may result in valuable effects upon analyte sorption, such as the observance of a double percolation threshold. Binary polymer blend sensors can be prepared from a variety of polymers at incrementally different blend stoichiometries. Instead of manually fabricating twenty blends of varying composition, a spray gun with dual controlled-flow feedstocks could be used to deposit a graded-composition polymer film across a series of electrodes. Such automated procedures allow extension of the sensor compositions beyond simple binary blends, thereby providing the opportunity to fabricate chemiresistors with sorption properties incrementally varied over a wide range. In the fabrication of many-component blends, a combinatorial approach aided by microjet fabrication technology is one approach that will be known to those skilled in the art. For instance, a continuous jet fed by five separate feedstocks can fabricate numerous polymer blends in a combinatorial fashion on substrates with appropriately patterned sets of electrodes. Multipla nozzle drop-on-demand systems (multiple nozzle continuous jet systems are not as prevalent because of their greater complexity) may also be used. In this approach, each nozzle would be fed with a different polymer, each dissolved in a common solvent. In this manner, a large number of combinations of 10-20 polymers can be readily fabricated.

The resistors can include nanoparticles comprising a central core conducting element and an attached ligand, with these nanoparticles dispersed in a semiconducting or conducting organic matrix. With reference to Table 2, various conducting materials are suitable for the central core. In certain embodiments, the nanoparticles have a metal core. Examples of metal cores include, but are not limited to, Au, Ag, Pt, Pd, Cu, Ni, AuCu and regions thereof. These metallic nanoparticles can be synthesized using a variety of methods. In one method of synthesis, a modification of the protocol developed by Brust et al. (the teachings of which are incorporated herein by reference), can be used. Using alkanethiolate gold clusters as an illustrative example, and not in any way to be construed as limiting, the starting molar ratio of $HAuCl_4$ to alkanethiol is selected to construct particles of the desired diameter. The organic phase reduction of $HAuCl_4$ by an alkanethiol and sodium borohydride leads to stable, modestly polydisperse, alkanethiolate-protected gold clusters having a core dimension of about 1 nm to about 100 nm. The nanoparticles range in size from about 1 nm to about 50 nm, but may also range in size from about 5 nm to about 20 nm.

In this reaction, a molar ratio of $HAuCl_4$ to alkanethiol of greater than 1:1 leads to smaller particle sizes, whereas a molar ratio of $HAuCl_4$ to alkanethiol less than 1:1 yield clusters which are larger in size. Thus, by varying the ratio of $HAuCl_4$ to alkanethiol, it is possible to generate various sizes and dimensions of nanoparticles suitable for a variety of analytes. Although not intending to be bound by any particular theory, it is believed that during the chemical reaction, as neutral gold particles begin to nucleate and grow, the size of the central core is retarded by the ligand monolayer in a controlled fashion. Using this reaction, it is then possible to generate nanoparticles of exacting sizes and dimensions.

In certain other embodiments, sensors are prepared as composites of "naked" nanoparticles and a semiconducting or conducting organic material is added. As used herein, the term "naked nanoparticles" means that the core has no covalently attached ligands or caps. A wide variety of semiconducting or conducting organic materials can be used in this embodiment. Preferred semiconducting or conducting materials are organic polymers. Suitable organic polymers include, but are not limited to, polyaniline, polypyrrole, polyacetylene, polythiophene, polyEDOT and derivatives thereof. Varying the semiconducting or conducting material types, concentration, size, etc., provides the diversity necessary for an array of sensors. In one embodiment, the conductor to semiconducting or conducting organic material ratio is about 50% to about 90% (wt/wt).

Sensor arrays allow expanded utility because the signal for an imperfect "key" in one channel can be recognized through information gathered on another, chemically or physically dissimilar channel in the array. A distinct pattern of responses produced over the collection of sensors in the array can provide a fingerprint that allows classification and identification of the analyte, whereas such information would not have been obtainable by relying on the signals arising solely from a single sensor or sensing material.

The general method for using the disclosed sensors, arrays and electronic noses, for detecting the presence of an analyte in a fluid, where the fluid is a liquid or a gas, involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising first analyte and a second, different resistance when the resistor is contacted with a second, different fluid.

An ideal detector array would produce a unique signature for every different analyte to which it was exposed. To construct such a system, it is necessary to include detectors that probe important, but possibly subtle, molecular parameters such as chirality. The term "chiral" is used herein to refer to an optically active or enantiomerically pure compound, or to a compound containing one or more asymmetric centers in a well-defined optically active configuration. A chiral compound is not superimposable upon its mirror image. Harnessing enantiomer resolution gives rise to myriad applications. For instance, because the active sites of enzymes are chiral, only the correct enantiomer is recognized as a substrate. Thus, pharmaceuticals having near enantiomeric purity are often many more times active than their racemic mixtures. However, many pharmaceutical formulations marketed today are racemic regions of the desired compound and its "mirror image." One optical form (or enantiomer) of a racemic region may be medicinally useful, while the other optical form may be inert or even harmful, as has been reported to be the case for thalidomide. Various methods exist which generate the correct enantiomer, including chiral synthesis, enzymatic resolution or some other means of obtaining the optically active compound. Due to the wide range of industrial applications, there is a growing interest in finding ways to resolve racemic regions into optically active isomers, or to synthesize enantiomerically pure compounds directly and rapidly monitor the efficiency of such processes. Chiral sensor elements could be part of a larger detector array that included non-chiral elements, thus broadening the discrimination ability of such arrays towards chiral analytes. Some of the elements can possess chiral feedstocks and/or chiral organic electrically conducting elements and/or chiral capping agents on conductive particles in order to detect chiral analytes through their distinct response pattern on an array of sensors. Suitable chiral resolving agents include, but are not limited to, chiral molecules, such as chiral polymers; natural products, such as, tartaric, malic and mandelic acids; alkaloids, such as brucine, strychnine, morphine and quinine; lanthanide shift reagents; chelating agents; biomolecules, such as proteins, cellulose and enzymes; and chiral crown ethers together with cyclodextrins. (see, E. Gassmann et al., "Electrokinetic Separation of Chiral Compounds," Science, vol. 230, pp. 813-814 (1985); and R. Kuhn et al., "Chiral Separation by Capillary Electrophoresis," Chromatographia, vol. 34, pp. 505-512 (1992)). Additional chiral resolving agents suitable for use in the present invention will be known by those of skill in the art. In this fashion, the sensors and sensor arrays would be useful in assessing which form of chirality, and of what enantiomeric excess, was present in an analyte in a fluid. Due to the presence of chiral moieties, many biomolecules, such as amino acids, are amenable to detection using the sensor arrays of the present invention. Plasticizers can also be used to obtain improved mechanical, structural, and sorption properties of the sensing films. Suitable plasticizers for use in the present invention include, but are not limited to, phthalates and their esters, adipate and sebacate esters, polyols such as polyethylene glycol and their derivatives, tricresyl phosphate, castor oil, camphor etc. Those of skill in the art will be aware of other plasticizers suitable for use in the present invention.

The plasticizer can also be added to an organic polymer forming an interpenetrating network (IPN) comprising a first organic polymer and a second organic polymer formed from an organic monomer polymerized in the presence of the first organic polymer. This technique works particularly well when dealing with polymers that are immiscible in one another, where the polymers are made from monomers that are volatile. Under these conditions, the preformed polymer is used to dictate the properties (e.g., viscosity) of the polymer-monomer region. Thus, the polymer holds the monomer in solution. Examples of such a system are (1) polyvinyl acetate with monomer methylmethacrylate to form an IPN of pVA and pMMA, (2) pVA with monomer styrene to form an IPN of pVA and polystyrene, and (3) pVA with acrylonitrile to form an IPN of pVA and polyacrylonitrile. Each of the example compositions would be modified by the addition of an appropriate plasticizer. More than one monomer can be used where it is desired to create an IPN having one or more copolymers.

In another embodiment, the sensor for detecting the presence of a chemical analyte in a fluid comprises a chemically sensitive resistor electrically connected to an electrical measuring apparatus where the resistor is in thermal communication with a temperature control apparatus. As described above, the chemically sensitive resistor(s) comprise regions of a conductive organic polymer and regions of a conductive material which is compositionally different than the conductive organic material. The chemically sensitive resistor provides an electrical path through which electrical current may flow and a resistance (R) at a temperature (T) when contacted with a fluid comprising a chemical analyte.

In operation, the chemically sensitive resistor(s) of the sensor for detecting the presence of a chemical analyte in a fluid provide an electrical resistance ($R_m$) when contacted with a fluid comprising a chemical analyte at a particular temperature ($T_m$). The electrical resistance observed may vary as the temperature varies, thereby allowing one to define a unique profile of electrical resistances at various different temperatures for any chemical analyte of interest. For example, a chemically sensitive resistor, when contacted with a fluid comprising a chemical analyte of interest, may provide an electrical resistance $R_m$ at temperature $T_m$ where m is an integer greater than 1, and may provide a different electrical resistance $R_n$ at a different temperature $T_n$. The difference between $R_m$ and $R_n$ is readily detectable by an electrical measuring apparatus.

As such, the chemically sensitive resistor(s) of the sensor are in thermal communication with a temperature control apparatus, thereby allowing one to vary the temperature at which electrical resistances are measured. If the sensor comprises an array of two or more chemically sensitive resistors each being in thermal communication with a temperature control apparatus, one may vary the temperature across the entire array (i.e., generate a temperature gradient across the array), thereby allowing electrical resistances to be measured simultaneously at various different temperatures and for various different resistor compositions. For example, in an array of chemically sensitive resistors, one may vary the composition of the resistors in the horizontal direction across the array, such that resistor composition in the vertical direction across the array remains constant. One may then create a temperature gradient in the vertical direction across the array, thereby allowing the simultaneous analysis of chemical analytes at different resistor compositions and different temperatures.

Methods for placing chemically sensitive resistors in thermal communication with a temperature control apparatus are readily apparent to those skilled in the art and include, for example, attaching a heating or cooling element to the sensor and passing electrical current through said heating or cooling element. The temperature range across which electrical resistances may be measured will be a function of the resistor composition, for example the melting temperature of the resistor components, the thermal stability of the analyte of interest or any other component of the system, and the like. For the most part, the temperature range across which electrical resistance will be measured will be about 10° C. to 80° C., preferably from about 22° C. to about 70° C. and more preferably from about 20° C. to 65° C.

In yet another embodiment, rather than subjecting the sensor to a direct electrical current and measuring the true electrical resistance through the chemically sensitive resistor(s), the sensor can be subjected to an alternating electrical current at different frequencies to measure impedance. Impedance is the apparent resistance in an alternating electrical current as compared to the true electrical resistance in a direct current. As such, the present invention is also directed to a sensor for detecting the presence of a chemical analyte in a fluid, said sensor comprising a chemically sensitive resistor electrically connected to an electrical measuring apparatus, said chemically sensitive resistor comprising regions of conductive organic material and regions of a conductive material compositionally different than said conductive organic material and wherein said resistor provides (a) an electrical path through said region of nonconductive organic polymer and said conductive material, and (b) an electrical impedance $Z_m$ at frequency $\theta_m$ when contacted with a fluid comprising said chemical analyte, where m is an integer greater than 1 and $\theta_m$ does not equal 0. For measuring impedance as a function of frequency, the frequencies employed will generally range from about 1 Hz to 5 GHz, usually from about 1 MHZ to 1 GHz, more usually from about 1 MHZ to 10 MHZ and preferably from about 1 MHZ to 5 MHZ. Chemical analytes of interest will exhibit unique impedance characteristics at varying alternating current frequencies, thereby allowing one to detect the presence of any chemical analyte of interest in a fluid by measuring $Z_m$ at alternating frequency $\theta_m$.

For performing impedance measurements, one may employ virtually any impedance analyzer known in the art. For example, a Schlumberger Model 1260 Impedance/Gain-Phase Analyzer (Schlumberger Technologies, Farmborough, Hampshire, England) with approximately 6 inch RG174 coaxial cables is employed. In such an apparatus, the resistor/sensor is held in an A1 chassis box to shield it from external electronic noise.

In still another embodiment of the present invention, one may vary both the frequency $\theta_m$ of the electrical current employed and the temperature $T_n$ and measure the electrical impedance $Z_{m,n}$, thereby allowing for the detection of the presence of a chemical analyte of interest. As such, the present invention is also directed to a sensor for detecting the presence of a chemical analyte in a fluid, said sensor comprising a chemically sensitive resistor electrically connected to an electrical measuring apparatus and being in thermal communication with a temperature control apparatus, said chemically sensitive resistor comprising regions of conductive organic material and regions of a conductive material compositionally different than said conductive organic polymer, wherein said resistor provides (1) an electrical path through said region of nonconductive organic polymer and said conductive material, and (2) an electrical impedance $Z_{m,n}$ at frequency $\theta_m$ and temperature $T_n$ when contacted with a fluid comprising said chemical analyte, where m and/or n is an integer greater than 1. For measuring impedance as a function of frequency and temperature, the frequencies employed will generally not be higher than 10 MHZ, preferably not higher than 5 MHZ. Chemical analytes of interest will exhibit unique impedance characteristics at varying alternating current frequencies and varying temperatures, thereby allowing one to detect the presence of any chemical analyte of interest in a fluid by measuring $Z_{m,n}$ at frequency $\theta_m$ and temperature $T_n$.

In another procedure, one particular sensor composition can be used in an array and the response properties can be varied by maintaining each sensor at a different temperature from at least one of the other sensors, or by performing the electrical impedance measurement at a different frequency for each sensor, or a combination thereof.

An electronic nose for detecting an analyte in a fluid is fabricated by electrically coupling the sensor leads of an array of differently responding sensors to an electrical measuring device. The device measures changes in signal at each sensor of the array, preferably simultaneously and preferably over time. Preferably, the signal is an electrical resistance, although it could also be an impedance or other physical property of the material in response to the presence of the analyte in the fluid. Frequently, the device includes signal processing means and is used in conjunction with a computer and data structure for comparing a given response profile to a structure-response profile database for qualitative and quantitative analysis. Typically such a nose comprises usually at least ten, often at least 100, and perhaps at least 1000 different sensors though with mass deposition fabrication techniques described herein or otherwise known in the art, arrays of on the order of at least one million sensors are readily produced.

In one mode of operation with an array of sensors, each resistor provides a first electrical resistance between its conductive leads when the resistor is contacted with a first fluid comprising a first chemical analyte, and a second electrical resistance between its conductive leads when the resistor is contacted with a second fluid comprising a second, different chemical analyte. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration or identity, i.e., the difference between the first and second electrical resistance of one sensor is different from the difference between the first second electrical resistance of another sensor.

In one embodiment, the temporal response of each sensor (resistance as a function of time) is recorded. The temporal response of each sensor may be normalized to a maximum percent increase and percent decrease in signal which produces a response pattern associated with the exposure of the analyte. By iterative profiling of known analytes, a structure-function database correlating analytes and response profiles is generated. Unknown analytes may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

The desired signals if monitored as dc electrical resistances for the various sensor elements in an array can be read merely by imposing a constant current source through the resistors and then monitoring the voltage across each resistor through use of a commercial multiplexable 20 bit analog-to-digital converter. Such signals are readily stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer.

Data analysis can be performed using standard chemometric methods such as principal component analysis and SIMCA, which are available in commercial software packages that run on a PC or which are easily transferred into a computer running a resident algorithm or onto a signal analysis chip either integrated onto, or working in conjunction with, the sensor measurement electronics. The Fisher linear discriminant is one preferred algorithm for analysis of the data, as described below. In addition, more sophisticated algorithms and supervised or unsupervised neural network based learning/training methods can be applied as well (Duda, R. O.; Hart, P. E. Pattern Classification and Scene Analysis; John Wiley & Sons: New York, 1973, pp 482).

The signals can also be useful in forming a digitally transmittable representation of an analyte in a fluid. Such signals could be transmitted over the Internet in encrypted or in publicly available form and analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in fluids is an important value-added component of the data.

20-30 different sensors is sufficient for many analyte classification tasks but larger array sizes can be implemented as well. Temperature and humidity can be controlled but because a preferred mode is to record changes relative to the ambient baseline condition, and because the patterns for a particular type and concentration of odorant are generally independent of such baseline conditions, it is not critical to actively control these variables in some implementations of the technology. Such control could be achieved either in open-loop or closed-loop configurations.

The sensors and sensor arrays disclosed herein could be used with or without preconcentration of the analyte depending on the power levels and other system constraints demanded by the user. Regardless of the sampling mode, the characteristic patterns (both from amplitude and temporal features, depending on the most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or nondisease, toxic or nontoxic chemical, good or bad polymer samples, fresh or old fish, fresh or contaminated air etc.). Analyte sampling will occur differently in the various application scenarios. For some applications, direct headspace samples can be collected using either single breath and urine samples in the case of sampling a patient's breath for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. The absorbent material of the fluid concentrator can be, but is not limited to, a nanoporous material, a microporous material, a chemically reactive material, a non-porous material and combinations thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof.

Breath samples can be collected through a straw or suitable tube in a patient's mouth that is connected to the sample chamber (or preconcentrator chamber), with the analyte outlet available for capture to enable subsequent GC/MS or other selected laboratory analytical studies of the sample. In other applications, headspace samples of odorous specimens can be analyzed and/or carrier gases can be used to transmit the analyte of concern to the sensors to produce the desired response. In still other cases, the analyte will be in a liquid phase and the liquid phase will be directly exposed to the sensors; in other cases the analyte will undergo some separation initially and in yet other cases only the headspace of the analyte will be exposed to the sensors.

Using the device of the present invention, the analyte can be concentrated from an initial sample volume of about 10 liters and then desorbed into a concentrated volume of about 10 milliliters or less, before being presented to the sensor array.

Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof. In these embodiments, the sample concentrator is wrapped with a wire through which current can be applied to heat and thus, desorb the concentrated analyte. The analyte is thereafter transferred to the sensor array.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

In a preferred embodiment of signal processing, the Fisher linear discriminant searches for the projection vector, w, in the detector space which maximizes the pairwise resolution factor, i.e., rf, for each set of analytes, and reports the value of rf along this optimal linear discriminant vector. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

To compute the rf, from standard vector analysis, the mean response vector, $x_a$, of an n-sensor array to analyte a is given as the n-dimensional vector containing the mean autoscaled response of each sensors, $A_{aj}$, to the $a^{th}$ analyte as components such that $$x_a = (A_{a1}, A_{a2}, \ldots A_{an})$$

The average separation, $|d|$, between the two analytes, a and b, in the Euclidean sensor response space is then equal to the magnitude of the difference between $x_a$ and $x_b$. The noise of the sensor responses is also important in quantifying the resolving power of the sensor array. Thus the standard deviations, $s_{a,d}$ and $s_{b,d}$, obtained from all the individual array responses to each of a and b along the vector d, are used to describe the average separation and ultimately to define the pairwise resolution factor as $$rf = d_w / \sqrt{(\sigma^2_{a,w} + \sigma^2_{b,w})}.$$

Even if the dimensionality of odor space is fairly small, say on the order of $10^1$, there is still interest in being able to model the biological olfactory system in its construction of arrays consisting of large numbers of receptor sites. Furthermore, even if a relatively small number (<10) of ideal sensors could indeed span odor space, it is not likely that such ideal sensors could be identified. In practice, correlations between the elements of a sensor array will necessitate a much larger number of sensors to successfully distinguish molecules. Furthermore, performance issues such as response time, signal averaging, or calibration ranges may require multiple sensors based on each material. Analysis of regions will add additional degrees of freedom if the components of the region are to be individually identified and will require large numbers of sensors. Fabrication of large numbers of sensors also enables the use of very powerful coherent signal detection algorithms to pull a known, but small amplitude, signal, out of a noisy background. Because of all of these issues, the number of sensors required to successfully span odor space in a practical device may rapidly multiply from the minimum value defined by the dimensionality of smell space.

The following examples are offered by way of illustration and not by way of limitation.

EXAMPLES

Polyaniline is a unique polymer whose properties have been studied extensively since its introduction twenty years ago. The partially reduced form of polyaniline, emeraldine (EM), exhibits a change in conductivity upon protonation, making it a valuable sensor material. Normally an insulating polymer, EM can be acid doped to yield the emeraldine salt (ES), a highly conductive polymer. If this doping takes place in the presence of a slightly acidic solvent, the conductivity is increased even further as pseudo-doping by the solvent promotes the adoption of a more highly linear configuration. Recently, hexafluoro-2-propanol (HFIP) has been introduced as a favorable solvent for processing of the emeraldine salt. HFIP is an acidic solvent with a low boiling point that dissolves ES prepared from a variety of sulfonic acid dopants. The pseudo-doping effects of HFIP are retained even after all of the solvent has been evaporated. Consequently, ES films processed from HFIP solutions are more conductive and exhibit increased linearity over films prepared from other solvents. The superior response of the polyaniline discussed in this report is attributed in part to these unique properties.

The response of sensors prepared from EM doped with dodecyl benzene sulfonic acid (DBSA) in HFIP solution has been studied in detail. These sensors exhibit an extremely large response ($\Delta R/R > 10000\%$ at 1% vapor pressure) for certain amines but a smaller resistance change ($\Delta R/R \sim 2\%$ at 1% vapor pressure) for other solvents. These sensors also appear to have detection limits in the parts per billion range, or lower, for amines. The mechanism of the resistance increase has been investigated using QCM measurements of mass uptake into the polymer film, which indicate that a percolation mechanism cannot be solely responsible for the extraordinarily large responses to amines. Measurement of the visible spectrum of films prepared from EM:DBSA (1:0: 5) in HFIP before and after exposure to amines exhibit a shift characteristic of deprotonation, as reported by Grummt, which corresponds to the color change from green to blue observed when the sensors are exposed to amines.

Example A

Preparation of Polyaniline Solutions:
Solutions were prepared using both ethane sulfonic acid (ESA) and dodecyl benzene sulfonic acid (DBSA), according to the following method. The sulfonic acid was dissolved in 10 mL HFIP. Emeraldine, which was generously donated by Ball and Kramer of the Kramer group at UCLA, was then added such that the molar ratio of polyaniline repeat unit to sulfonic acid was 1:0.5 and the total weight of polyaniline and acid was between 0.08 g and 0.1 g. This mixture was then sonicated without heating, for ten minutes. Some polyaniline remained undissolved at this point, but the majority was contained in the resulting dark blue solution. Carbon black (Black Pearls 2000, Cabot) was then added in a weight: weight ratio of 20:80 with the acid doped polymer. The mixture was again sonicated for ten minutes to create a suspension of carbon black in the polymer solution. For example, to prepare the EM:DBSA (1:0.5):CB (80:20) solution 0.0807 g DBSA was dissolved in 10 mL HFIP. EM (0.0415 g) was then added and the mixture sonicated ten minutes. Carbon black (0.0280 g) was added to the solution, and the mixture was again sonicated ten minutes. Solutions were prepared by the same method such that the acid: polymer ration was 1:1. Materials were from Aldrich unless otherwise notes.

Example B

Preparation of Sensors:
Glass substrates were prepared by deposition of two bands of gold separated by 5 mm, onto commercial 7.5 cm×2.5 cm glass slides.

The slides were then cut into strips to produce substrates that were approximately 0.7 cm×2.5 cm each with two gold leads separated by a mm gap. Sensors were prepared by spin coating the solutions described above, immediately after they were prepared onto the substrates. To do so, the substrate was saturated with solution, then spun at approximately 1200 rpm for about thirty seconds. All visible solvent was allowed to evaporate, then the resistance across the sensor was measured. The process was repeated if necessary to obtain sensors with resistance on the order of $10^5$ ohms. Sensors were then placed under airflow for at least twenty-four hours to ensure that all HFIP had been evaporated before use. Finished sensors were yellow to green in color, depending on the acid and doping ratio used.

Example C

Apparatus for Measurement of Response to Vapors:
In order to measure the response of the sensors to solvents at various partial pressures, a bubbler apparatus was prepared using standard glassware. A ground glass stopper equipped with an exit side arm and a long glass tube terminating in a filter frit was inserted into a large test tube that held the solvent to be detected. Carrier gas consisting of oil-free compressed air from the general lab source was passed through a mass-flow controller and into the solvent by way of the filter frit. The resulting solvent-saturated gas flowed through the side arm to a tube where it was diluted with a controlled flow of pure carrier gas to the desired partial pressure and then introduced into the sensor chamber. The chamber consisted of a small metal box equipped with two electrical contacts attached to wires that ran out of the chamber through gas-tight passages to a digital multimeter. The entire box was sealed closed with Teflon tape while resistance measurements were taken. Gas flow rates were controlled using a PC attached to the mass-flow controllers.

Example D

Apparatus for Low-Concentration Measurements:
The bubbler apparatus described above did not permit accurate measurements of partial pressures below about 0.1% vapor pressure. Therefore, a separate apparatus was designed to investigate the detection limits of the polyaniline sensors. A 1 L glass jar with Teflon lined top equipped with a septum-sealed port was used as the "dilution jar." The Teflon lined top of a second 1 L glass jar was equipped with three septum-sealed ports. Electrical lead wires equipped with flat-jawed alligator clips were threaded through two of the septa, and the third septum was used as an injection port. A sensor was attached to the two alligator clips so that its resistance could be monitored by a digital ohmmeter to which the wires were attached. To obtain low concentrations of analyte, headspace concentrations of analyte vapor were injected into the dilution jar using a gas-tight syringe. The barrel of the syringe was then flushed with air for five minutes, then a sample of gas from the dilution jar was injected to the jar containing the sensor, producing a low concentration of analyte in the sensor jar. The jar lids were sealed in place with Teflon tape during the experiments.

Example E

Measurements:
In order to observe the response of the sensors to various vapors, the dc resistance of the sensors was measured as a function of time using Keithley multimeter. Measurements were performed using a simple two-point configuration since it had been determined previously that the vapor-induced change in contact resistance was minimal compared to the vapor-induced resistivity change of the polymer film. In a typical experiment, a sensor was placed in the sensor chamber and attached to its metal contacts. The chamber was then sealed shut and background airflow was initiated through the chamber. Resistance across the sensor was measured for about three minutes to obtain a baseline, then air flow through the solvent was initiated such that solvent vapors of the concentration chosen for the experiment flowed across the sensor for about three minutes. The airflow through the solvent was then turned off, returning the airflow through the sensor chamber to background air. Resistance was recorded for five to ten minutes of recovery time. The process could then be repeated to begin the next experiment. Prior to experiments testing the sensor response to a solvent, the sensor was generally "aged" by exposure to typical solvents such as methanol, tetrahydrofuran (THF), chloroform, and water to avoid recording initial swelling effects and hysteresis as true response. Solvent concentrations were calculated in terms of fractional vapor pressure. This factor is determined by division of the partial pressure of solvent by the vapor pressure of the solvent under ambient conditions, as reported in the literature. Resistance changes were calculated by division of the change in resistance by the baseline resistance ($\Delta R/R$), since this value is consistent from sensor to sensor. Both factors are generally reported as percentages.

Figure 4:
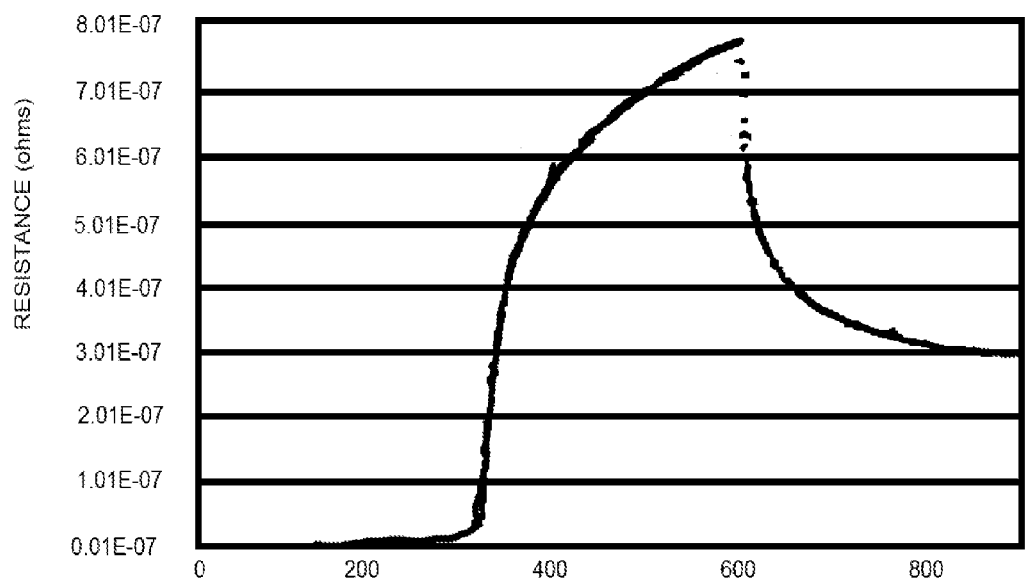
FIG. 4 shows a plot of the resistance of a sensor prepared from EM:DBSA(1:0.5 molar) ratio):carbon black (80:20 w/w) solution in HFIP. The film was deposited onto a glass slide substrate. The sensor was exposed to triethylamine at 0.5% of its vapor pressure, producing a resistance increase. The response is orders of magnitude larger than any seen from sensors prepared from insulating polymer-carbon black composite films.
Figure 5:
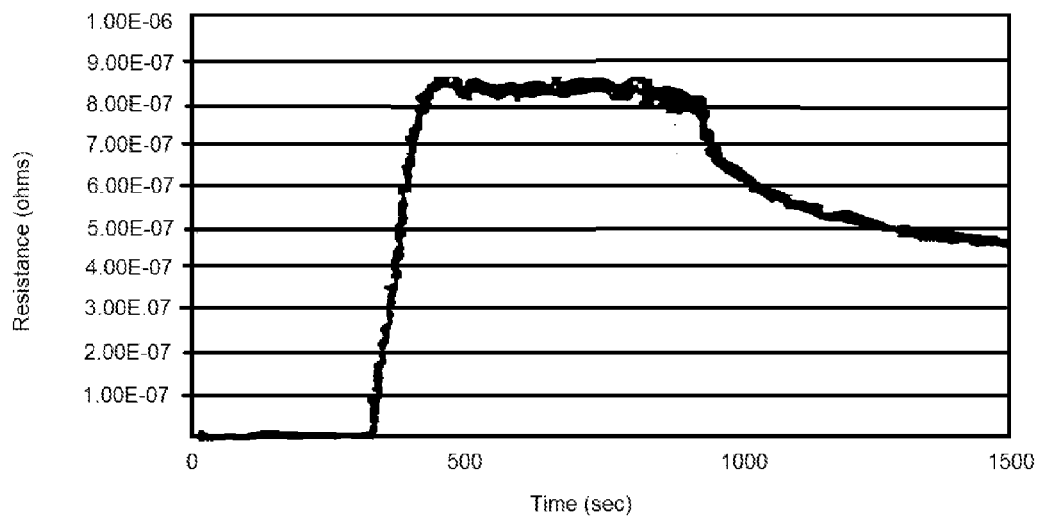
FIG. 5 shows a plot of the resistance of a sensor prepared from EM:DBSA(1:0.5 molar) ratio):carbon black (80:20 w/w) solution in HFIP. The film was deposited onto a glass slide substrate. The sensor was exposed to butylamine at 0.5% of its vapor pressure, producing a resistance increase. The response is orders of magnitude larger than any seen from sensors prepared from insulating polymer-carbon black composite films.

Results:

The response of EM-DBSA (1:0.5):CB (80:20) sensors to both typical solvents and to amines was investigated in detail. Sensors which were not less than twenty-four hours old and had been aged by exposure to headspace of typical solvents exhibited reproducible responses of 0.5%-5% $\Delta R/R$ at 1% vapor pressure for typical solvents (FIG. 5). The response for these same sensors to triethylamine ranged from 800%-1400% $\Delta R/R$ at 0.5% vapor pressure (FIG. 4). The response to triethylamine was only partially reversible and decreased by about 20% for subsequent exposures. The response of these sensors to butylamine ranged from 9000%-90000% $\Delta R/R$ at 0.5% vapor pressure (FIG. 5). This response was also only partially reversible and decreased for subsequent exposures. Occasionally, especially for sensors that had been prepared close to the time of exposure, after exposure to concentrated amine, subsequent responses become negative, both for amines and typical solvents. Trends of response were similar for EM-ESA (1:1):CB (80:20) sensors were similar, although the magnitude of response was not as large. Sensors prepared from EM-ESA (1:0.5):CB (80:20) and EM-DBSA (1:1):CB (80:20) exhibited very poor responses, to both amines and more typical solvents. For this reason, the EM-ESA (1:0.5):CB (80:20) sensors were used for most of the testing.

Figure 6:
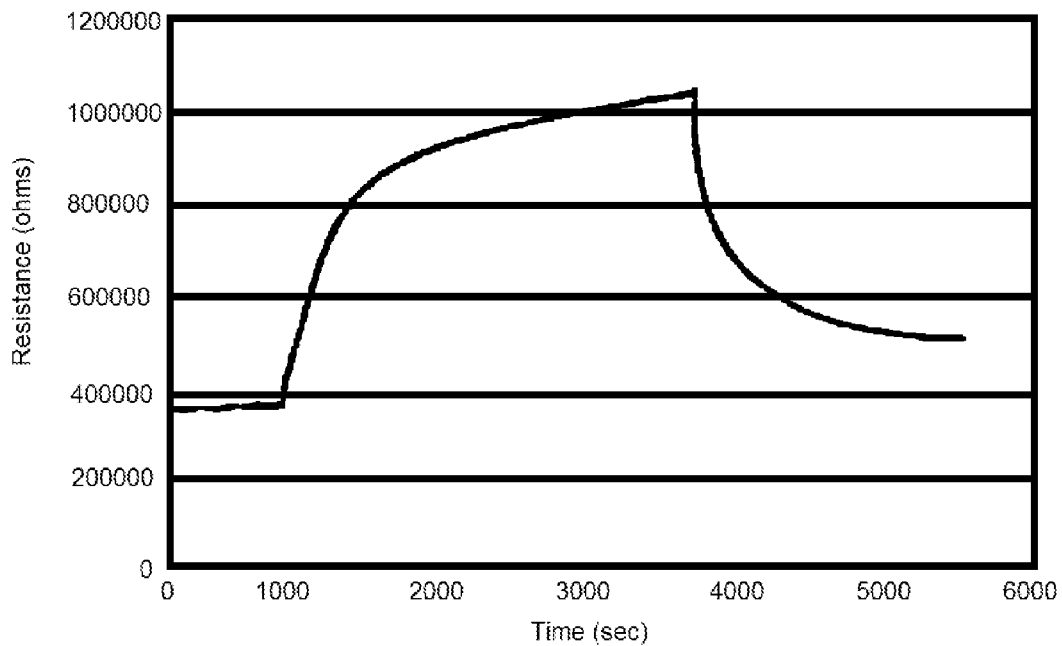
FIG. 6 shows a plot of the resistance (ohms) vs. Time (seconds) for a sensor prepared from EM:DBSA(1:0.5 molar) ratio):carbon black (80:20 w/w) solution in HFIP. The film was deposited onto a glass slide substrate. The sensor was exposed to cadaverine at 0.6 ppm, producing a resistance increase. The response corresponds to a detection threshold of 1 part in $10^{11}$ if the response remains linear with concentration.

It was of interest to determine whether the large amine response of the EM-DBSA (1:0.5):CB (80:20) sensors would continue down to low concentrations. It was determined that if the sensor response were linear with concentration, butylamine would have a detection threshold near one part in $10^{11}$. Low concentration experiments were performed using the apparatus described earlier. They showed a 3.08% $\Delta R/R$ at 86 ppb for butylamine. While this is an excellent magnitude of response for such a low concentration, it implies a detection threshold closer to one part in $10^{10}$. This may indicate that the sensor response is not linear with concentration, or it may indicate a flaw in the experimental apparatus. It is likely that analyte molecules could escape the dilution jar or adhere to surfaces during the waiting period for flushing of the syringe. At low concentrations, this type of error would make a large difference in response. Performing low concentration experiments in conjunction with a flame ionization detector would more accurately determine the actual concentration of butylamine incident on the sensor, but this has not yet been accomplished. Similar experiments were performed using cadaverine (1,4-diaminobutane), an analyte which is of interest both because it is a diamine and because of its presence as a breakdown product of rotting foods. At 0.6 ppm, a 194% $\Delta R/R$ was observed for cadaverine, indicating a detection threshold near one part of $10^{11}$ if linearity of the response can be assumed (FIG. 6). Lower concentrations of cadaverine could not be obtained using the current experimental apparatus.

Figure 7:
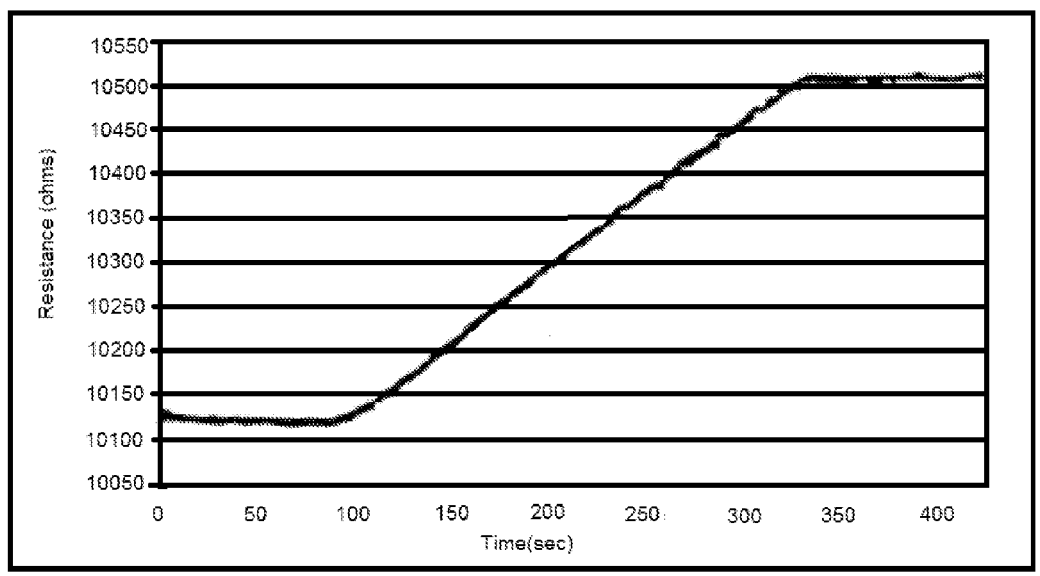
FIG. 7 is a plot of the resistance of a sensor prepared from Nafion117:carbon black (80:20 w/w). The film was deposited onto a glass slide substrate. The sensor was exposed to butylamine at 0.5% of its vapor pressure, producing a resistance increase. This response is much smaller than the response of the EM:DBSA(1:0.5):CB(80:20) sensors indicating that the Nafion sensors do not exhibit a large response to amines.

A variety of experiments were performed to elucidate the response mechanism of the acid doped emeraldine (ES) sensors. It was hypothesized that the large response to amines was due to a very strong acid-base interaction between the polymer and the airborne amine. This strong affinity would cause unusually large amounts of analyte to partition into the polymer, causing a large increase in resistance due to a percolation mechanism. This hypothesis was tested by two experiments. The first was simply a comparison of the response to the EM-DBSA sensors to sensors prepared from another very strong acid polymer, Nafion117. Nafion is a perflorinated ion exchange polymer with a Teflon backbone and is considered to be a very strong acid, comparable to 85% sulfuric acid. A solution was prepared from Nafion117, 5% acids in water (Aldrich) with carbon black in an 80:20 weight:weight ratio. This solution was spin coated onto standard glass substrates and the sensors were allowed to dry for at least 24 hours. The response of a typical Nafion117:CB (80:20) sensor to butylamine at 0.5% vapor pressure is shown in FIG. 7. The response is small and completely irreversible, unlike that of the acid-doped emeraldine sensors. This result indicates that simple acid-base mechanics cannot be solely responsible for the unusually large response of the EM-DBSA sensors to amines.

Figure 8:
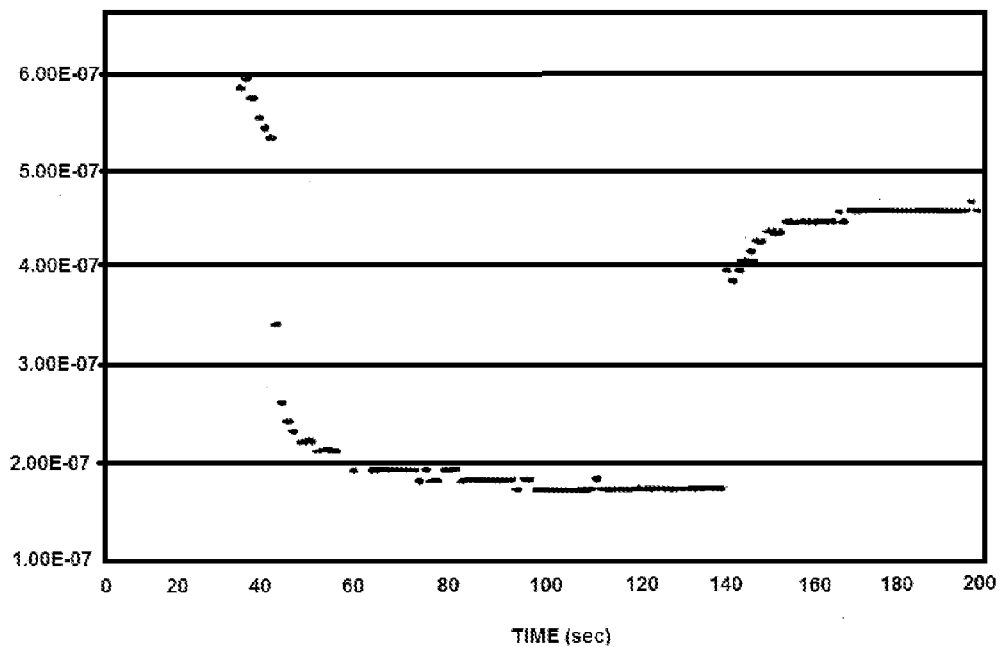
FIG. 8 shows a plot of frequency vs time recorded for a quartz crystal coated with EM:DBSA (1:0.5 mole ratio):carbon black (80:20 w/w) solution in HFIP. (A) the crystal was exposed to acetone at 1% of its vapor pressure causing a frequency change of 28 Hz, corresponding to a calculated mass uptake of 25.3 ng. (B) the crystal was exposed to butylamine at 1% of its vapor pressure causing a frequency change of −441 Hz, which corresponds to a calculated mass uptake of 399 ng.
Figure 8:
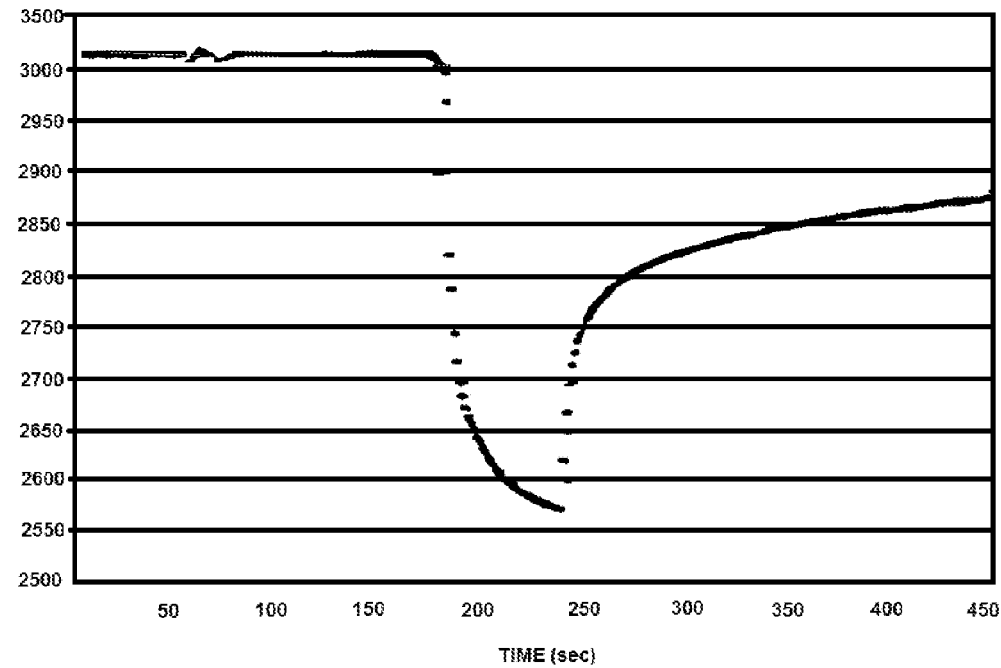
Figure 9:
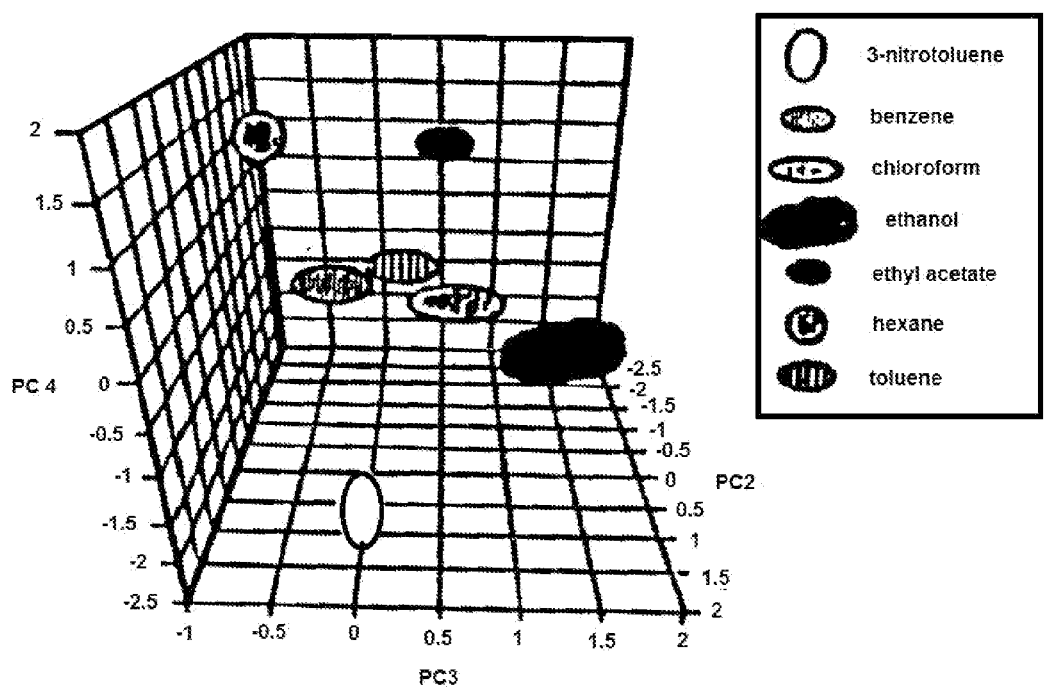
FIG. 9 shows a component representation of the data from a sensor array showing the successful resolution of 1 ppm nitrotoluene from several other common organic vapors in air.
Figure 10:
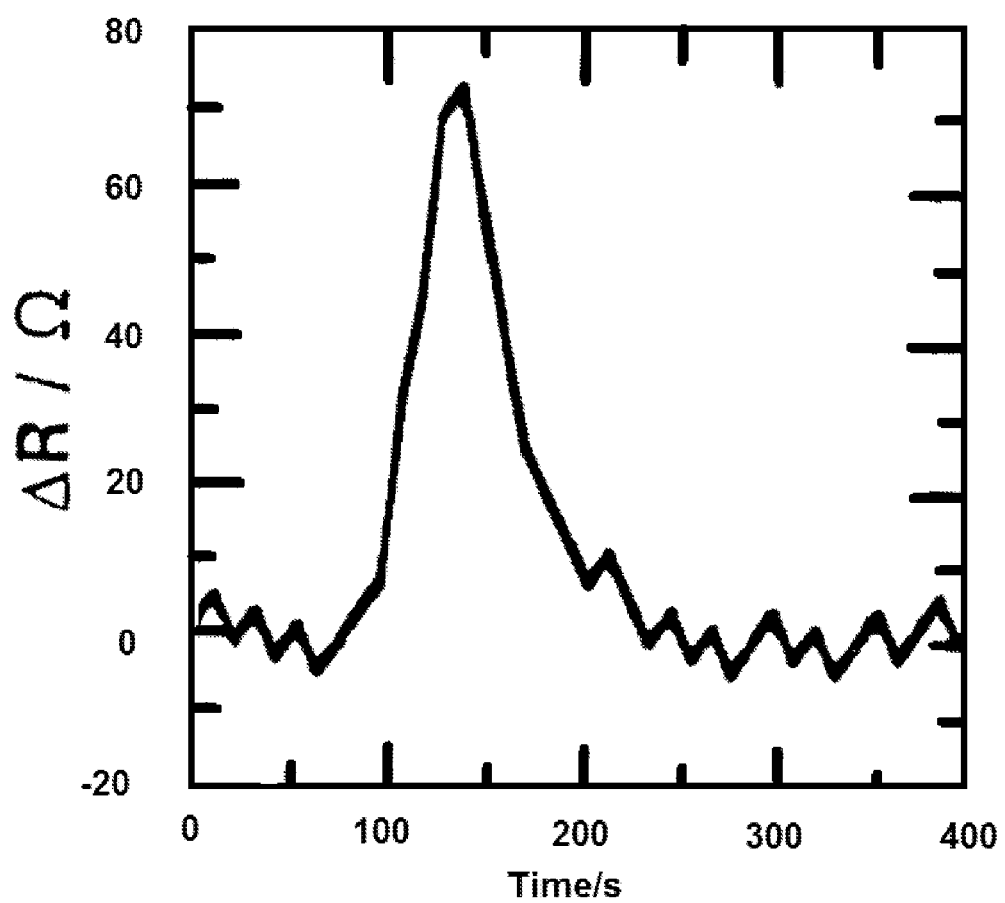
FIG. 10 shows the signal of an unoptimized poly (ethylene-co-vinylacetate)-carbon black composite to 883 ppb nitrotoluene in air.

A second test of the percolation threshold theory was performed by measuring the amount of analyte that is absorbed into the polymer film during a typical exposure. This was done using a quartz crystal microbalance (QCM). A commercial quartz crystal slide was coated with the EM-DBSA (1:0.5):CB (80:20) solution used to prepare the sensors, using the same method of spin coating. The film was allowed to dry for several days. The quartz crystal was exposed to pure air, then air with solvent vapors, then pure air again for each solvent investigated. The frequency response of the crystal was recorded during this procedure, just as the resistance response of the sensors was recorded in previous experiments. Plots of frequency vs. time were obtained, which appear strikingly similar to the plots of resistance vs. time obtained in previous experiments (FIG. 8). The change in the mass of the polymer film was determined from the observed frequency change using the Sauerbrey equation:

$$\Delta f = -2\Delta m\, n f_o^2 / (A\sqrt{\mu_q \rho_q})$$

The mass change was assumed to be due to partitioning of analyte into the polymer film. For typical solvents, such as acetone, toluene, and 1-butanol, the ratio of moles of analyte partitioned into the polymer per mole of polymer repeat unit was between 0.010 and 0.020. For butylamine, this factor was 0.17; about ten times as much amine was absorbed into the polymer as normal solvents. The mass change was also only partially reversible, indicating that some analyte remained in the polymer for an extended period of time. From these results it was determined that an elevated amount of amine partitioned into the polymer film, but not enough to account for the 10.000-fold increase in the % ΔR/R for amines over typical solvents. Therefore, the majority of the response is not accounted for by a percolation mechanism.

The mechanism of the large amine response must be directly related to the ES itself since other strong acid-carbon black sensors do not exhibit similar behavior. It was proposed that the polymer conductivity is disrupted by deprotonation by amines. A look at the spectral properties of the polymer film indicates that exposure to vapor-phase amines does in fact deprotonate the ES. A color change was observed when the sensors were exposed to amines, such that the film color changed from teal green to navy blue. A corresponding shift in the absorbance peak at 740 mm to 650 mm was observed in the optical spectrum of the film, measured using a Hewlett Packard 8452A spectrophotometer. This shift is associated to deprotonation of the emeraldine salt, as reported by Grummt, who studied the spectrum of EM case from HFIP and observed a shift of the peak from 750 mm to pH 2 to 575 to pH 10. This observation confirms that amines act to deprotonate the acid-doped emeraldine polymer.

Sensors prepared from emeraldine doped with DBSA consistently exhibit a response to amines which is several orders of magnitude larger than any observed from conventional polymer-carbon black sensors. At the same time, the EM-DBSA sensors respond to common solvents, making them more widely useful as part of a sensing array. Although the response to amines is generally irreversible, experiments at very low concentrations showed a tendency towards complete reversibility such that sensors could in some cases be reused. The acid-doped polyaniline sensors to amines is linked to the transformation of the polymer structure upon deprotonation. A look at the structure of emeraldine explains the large increase in the resistance of the polymer film upon deprotonation by an amine. As mentioned previously, the emeraldine form of polyaniline is an insulating polymer with the following structure (left):

polymer is caused by partitioning of solvent molecules into the film. The solvent used in preparing the polymer solutions, HFIP, has been shown to produce a more linear structure of polyaniline than other solvents, causing enhanced conductivity through the polymer. A deformation of this linear structure caused by adsorption of solvent molecules might cause permanent changes in the resistivity of the polymer. It still remains to be studied whether this type of percolation mechanism is involved in the sensors' response.

There are a wide variety of applications for amine sensitive sensors. They play a key role in the development of an electronic nose, providing extra sensitivity to amines which is characteristic of the human system. The low detection limits for amines make these sensors excellent for use in the food industry, where early detection of decay can improve quality and safety. Patients of certain diseases, such as cholera and lung cancer, excrete elevated levels of amines making it possible to diagnose the disease by detecting the biomarkers. The use of an electronic nose to recognize disease in patients' metabolites would provide an excellent non-invasive method of diagnosis of disease. The sensors are also useful as a part of an electronic nose array used to detect more general unknowns, since they will both signal the presence of amines and provide useful signal for other classes of compounds.

Emeraldine salt/carbon black solutions were prepared by first dissolving the emeraldine base (Polysciences, Inc.) into hexafluoroisopropanol. Sulfonic acid (reported as the mole ratio of polyaniline repeat to sulfonic acid) was then added (Hopkins, 1996) (Hopkins, 1998) and then sufficient carbon black was introduced to produce a suspension that was 20% by weight carbon black and 80% by weight polymer, excluding the weight of the solvent. The solution was then sonicated for twenty minutes to disperse the carbon black and a film was deposited onto glass substrates that had two gold contact pads separated by a 1 mm gap. Two point resistance measurements of the resulting conductive composite films were carried out

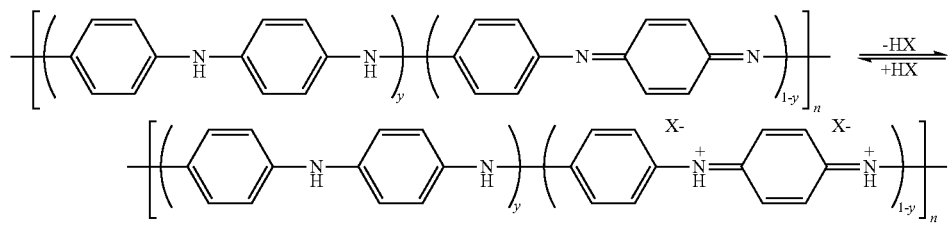

When emeraldine is protonated in a 1:0.5 molar ratio of polymer repeat unit to acid molecule, the protons attack preferentially at the imine sites, producing the structure on the right, a highly conductive polaron lattice in which all of the rings are equivalent. Thus, deprotonation of the ES breaks up these conductive bands, causing a large increase in the resistance of the polymer film. This mechanism appears to be responsible for the majority of the resistance increase observed upon exposure of acid-doped emeraldine sensors to amines.

The extent to which a percolation-type mechanism is responsible for the resistance increase of the ES sensors is still undetermined. It is possible that a minor part of the resistance increase of the sensors upon exposure to amines is in fact due to a decrease in conductivity through the carbon black particles. This is also the proposed mechanism for the response of the sensors to more common solvents. Also unknown is whether a change in the three-dimensional structure of the using a Keithley 2002 digital multimeter connected to the two Au contact pads. Streams of analyte vapors were generated using an apparatus that has been described above, while static and dynamic headspace experiments were performed in using conventional methods, as displayed above, these materials produce a million-fold increase in sensitivity, to the 1-10 ppt level, in air, for biogenic amines relative to the signals for analogous alcohols or to the signals for these amines produced on sensors that do not contain these specifically-designed conductive phases and which are comprised of conductor/insulator composites and arrays thereof that have been previously disclosed in the literature (FIG. 8).

The specific type of amine can be identified by fabricating an array of polyaniline based composite sensors, each having carbon black as the conducting component of the composite, and varying the counterion in each element of the array and/or including a variable additional insulating organic component in the composite, so that a differential response pattern is produced over the array of sensors (FIG. 11). Through this approach we have demonstrated the ability to classify and separate many prototype amines at very low concentration levels. In this fashion, we can take advantage of the power of pattern recognition strategies for analyte identification and classification of the amines at low concentration levels. The remainder of the array elements, made from carbon black sensors or other sensors, then provide information on the other, non-amine compounds in the same analyte sample.

Figure 11A:
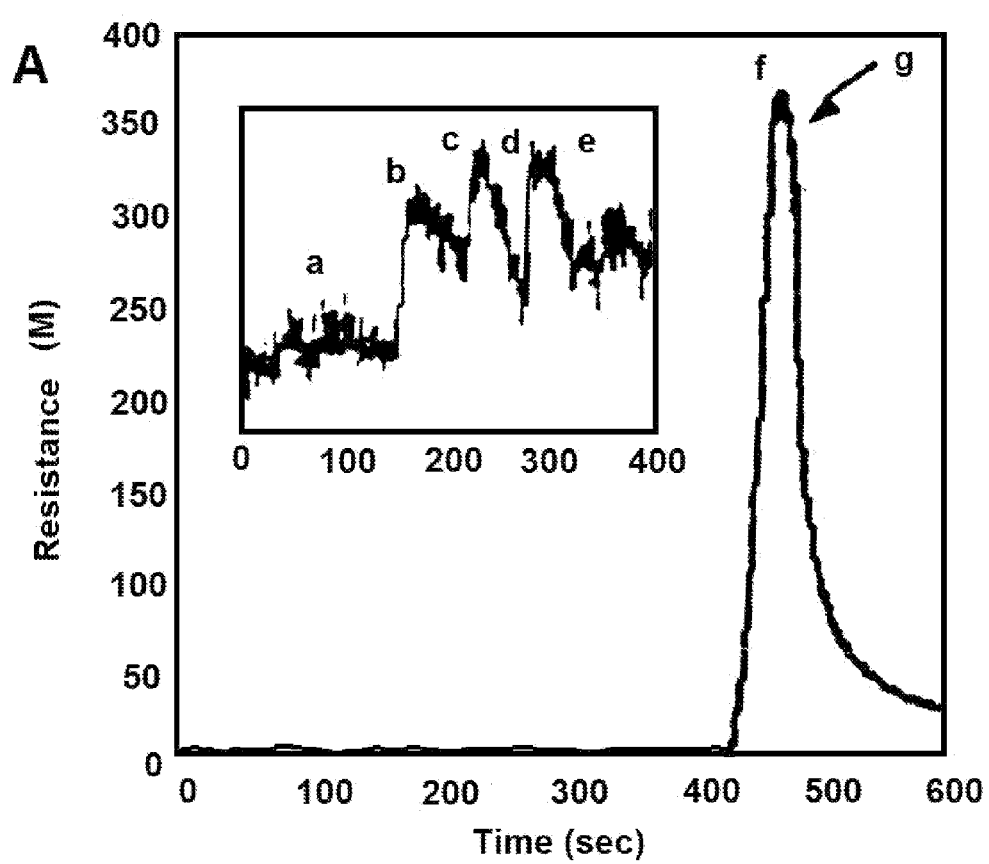
FIG. 11*a* shows a response pattern of an EM-DBSA(1:0.5)/CB (80:20) detector exposed to water (a), acetone (b), methanol (c), ethylacetate (d), butanol (e), and butylamine (f), all at 0.05% of their saturated vapor pressure. The scale on the ordinate of the inset is magnified by $10^6$ relative to the ordinate scale in the main figure. At point, (g), the sensor was removed from the chamber.

FIG. 11a represents a series of dynamic headspace exposures (performed by injecting 1 ml of saturated gas into a 2000 ml sealed glass container fitted with a magnetically controlled stirring fan) of the ES-DBSA(1:0.5)/CB detector to water (14.7 ppm), acetone (145 ppm), methanol (79 ppm), ethylacetate (59 ppm), butanol (4 ppm) and butylamine (58 ppm) each at the same activity (0.05% of the saturated vapor pressure). The responses defined as were calculated to be 0, 0.0018, 0.0012, 0.0015, 0, and $2.25 \times 10^3$, respectively. Thus, the response of the detector is approximately six orders of magnitude greater upon exposure to butylamine compared to the other five nonamine analytes. This experiment also demonstrates that the sensitivity of the sensor to water is at least six orders of magnitude worse than that to butylamine, which is pertinent for the use of the detector in a disease breathalyzer since water is one of the major constituents of expired breath.

Figure 11B:
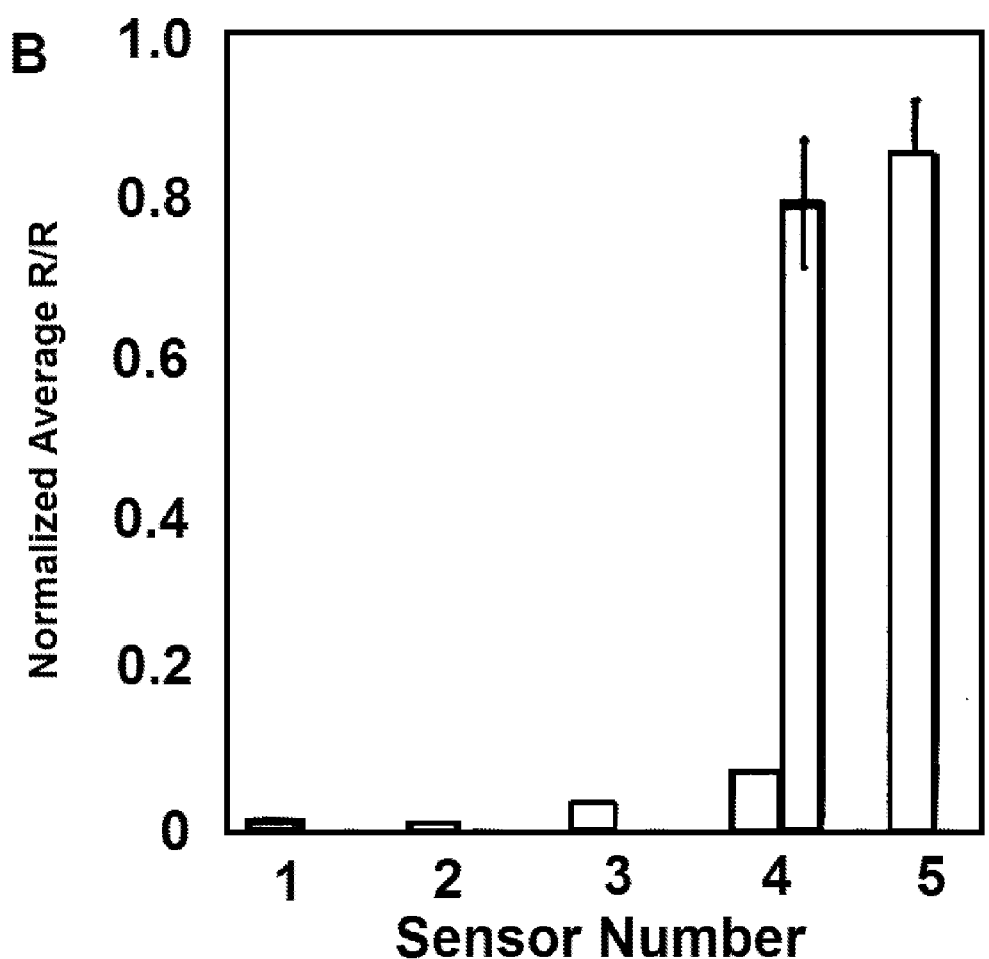
FIG. 11*b* shows a detector array pattern to the exposure of aniline (shaded) and butylamine both at the same activity (5% of their saturated vapor pressure). For aniline the detector responses were normalized using the maximum raw data response from sensor number 5 (ΔR/R=19.26) and for butylamine the responses were normalized using the maximum raw data response from sensor number 4 (ΔR/R=86,340).

FIG. 11b shows the response pattern generated for the exposure of the polyaniline composite sensor array to butylamine (BuA) and to aniline (Ani), each at the same activity (5% of their saturated vapor pressure). This detector array consisted of five different polyaniline detectors comprised of either a different sulfonic acid to dope the polymer or a different ratio of acid dopant to polymer in the sensor composite film. The responses are defined as the maximum differential resistance response relative to the baseline resistance ($\Delta R/R_b$) normalized with respect to the largest response across the five detector array for each separate analyte. Normalization was carried out in order to remove the concentration dependence in the data. The values are shown as the average of five copies of each detector to one exposure to the analyte. The ability of the detector array to discriminate between these two amines was quantitatively determined using the resolution factor (rf), obtained by projection of data cluster centroids onto a vector, w, and calculated from the equation:

$$rf = d_w/\sqrt{(\sigma^2_{a,w} + \sigma^2_{b,w})},$$

where $d_w$ is the distance between cluster centroids and both $\sigma^2_{a,w}$ and $\sigma_{b,w}$ are the projected standard deviations for the two different solvent data clusters, respectively. The resolution factor using the normalized data and the Fisher linear discriminant, in which the vector is not confined to connect the means of the data centroids but instead is allowed to optimize the rf value, was calculated to be 5,386 (where a resolution factor of 3 corresponds to a 98% probability of correctly identifying one analyte from the other). High discrimination has been observed for many biogenic amines in this fashion. In this test case, the analytes were essentially perfectly separated from each other based on their distinctive patterns on the detector array.

Figure 2:
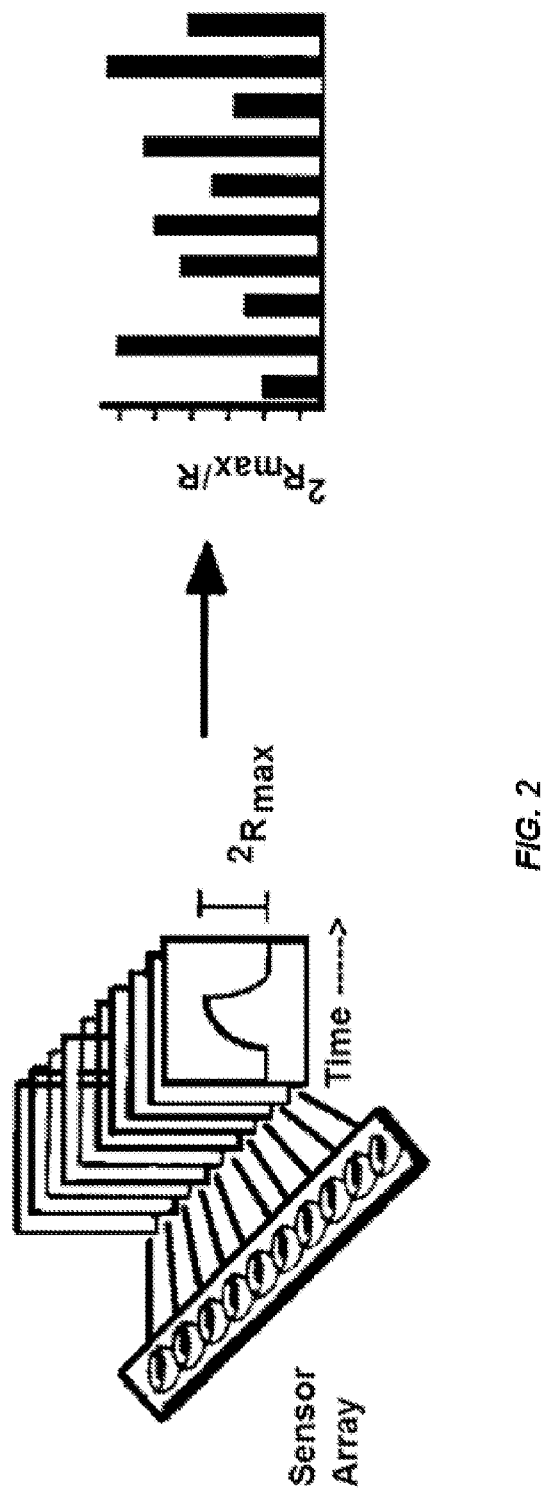
FIG. 2 shows a schematic and data derived from an array of broadly-cross reactive sensors in which each individual sensor responds to a variety of odors, but the pattern of differential responses across the array produces a unique pattern for each odorant.
Figure 3:
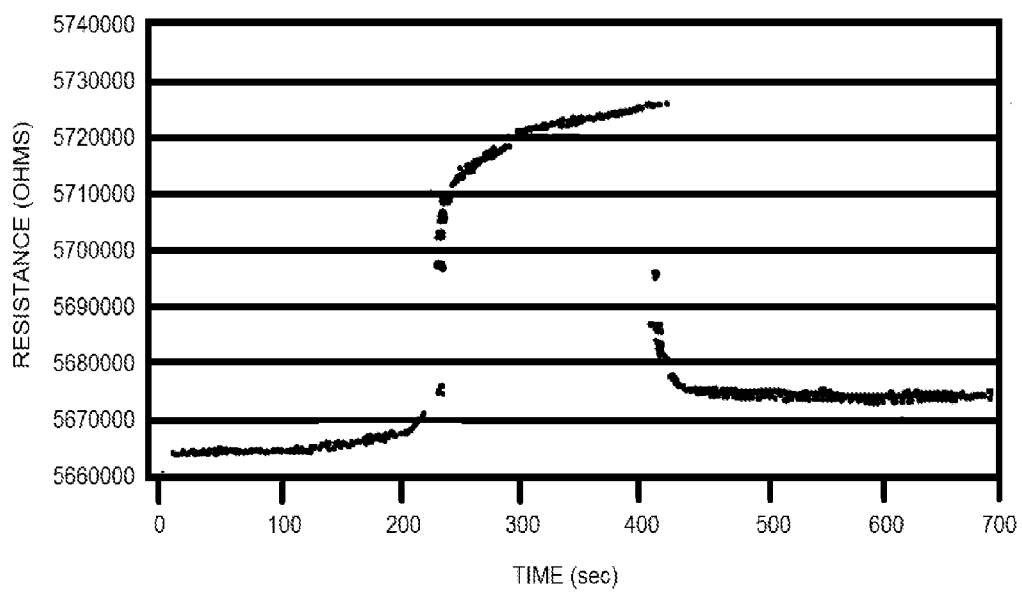
FIG. 3 shows a plot of the resistance of a sensor prepared from EM-DBSA (1:0.5 molar ratio):carbon black (80:20 w/w) solution in hexafluoroisopropanol (HFIP). The sensor was exposed to butanol at 1% of its vapor pressure, producing a resistance increase.

The detection thresholds, defined as the response required to obtain a signal to noise ratio of 3, were experimentally determined via static headspace exposures using an ES-DBSA(1:0.5)/CB composite film. These detection limits were 10 parts per trillion (ppt) for butylamine and 1 ppt for cadaverine. For comparative purposes, the human detection threshold for butylamine has been reported to be between 0.1 and 1 ppm and pristine emeraldine salt chemiresistive detectors have been reported to have detection thresholds of 1 ppm to ammonia. Furthermore, the ES-DBSA(1:0.5)/CB responses were pseudo-reversible (see FIG. 2) at high butylamine concentrations (between 50 parts per million and 1 part per thousand), but were reversible to exposures of butylamine at vapor phase concentrations between 10 ppt and 700 ppb.

To quantify the sorption behavior of these composites, a quartz crystal microbalance (QCM) with a 10 MHZ resonant frequency was used to assess the mass uptake characteristics of butylamine, butanol and acetone onto a ES-DBSA (1:0.5)/CB composite film. The response to both butanol and acetone was rapid (2 seconds to achieve 100% of the response) and reversible; whereas, the response to butylamine was slower (10 seconds to achieve 80% of the response) and pseudo-reversible. Using the Sauerbrey equation and assuming that modulus changes in the film are minimal, the mass uptake for acetone, butanol and butylamine was calculated to be within a factor of 10 of each other. Thus, although the sorption favors amines relative to acetone, the sorption effect can only account for a factor of $~10^1$ out of the $~10^6$ enhancement in sensitivity of these composites to amine analytes.

Evidence supporting a change in the conductivity of the polymer component of the system was obtained using UV-visible spectrophotometry during the exposure of the ES-DBSA(1:0.5)/CB detector to butylamine. The spectrum for the detector before to butylamine was identical to that previously reported for the emeraldine salt. In contrast, after the injection of 1 ml of saturated butylamine vapor into a sealed 4.5 cm$^3$ quartz cuvette, the ES/CB film displayed absorption maxima at both 340 nm and 660 nm. These two maxima have previously been attributed to both the p to p* transition electrons of the benzene delocalized onto nitrogen atoms of the amine and to the excitation from the highest occupied molecular orbital (HOMO pb) of the benzoid ring to the lowest unoccupied molecular orbital (LUMO pq) of the localized quinoid ring, for the emeraldine base, respectively.

The enhanced sensitivity obtained to this class of compounds indicates the flexibility in detector design that is made possible by using conductor/semiconductor or conductor/conductor composites as elements of sensor arrays. Obtaining analogous sensitivity improvements for these classes of compounds using polymer-coated surface acoustic wave resonators would require introduction of amine-selective binding sites into the polymer film or would require obtaining very large amplification effects due to extreme changes in the acoustic modulus of the polymer film upon analyte sorption. Mass-based detectors, such as QCM's or micromachined cantilevers coated with polymer films could not display the enhanced sensitivity reported here, given the small increase in sorption properties exhibited by these types of films for amine vapors. The superior sensitivity of these materials now means that it is possible to match or exceed the sensitivities of organoleptic panels to these chemically-important components of a variety of odorants in one of the specific embodiments illustrated in this work.

Example F

Sensor Preparation: Poly (3-hexylthiophene)/carbon black

Detector 1—A solution of neutral regioregular poly(3-hexylthiophene) was prepared by dissolving 0.2 g in 20 milliliters of benzene. Fifty mg of Carbon black was then added and the solution was sonicated for approximately 10 minutes.

Sensors were prepared by spin casting from this solution onto glass/gold substrates at a spin rate of 1000 rpm.

Poly(3-codecylthiophene)/carbon black

Detector 2—A solution of neutral regioregular poly(3-dodecylthiophene) was prepared by dissolving 0.1 g in 10 milliliters of chloroform. Twenty-five mg of Carbon black was then added and the solution was sonicated for approximately 10 minutes. Sensors were prepared by spin casting from this solution onto glass/gold substrates at a spin rate of 1000 rpm (3 coats).

Poly(bis(2,7-(3,4-ethylenedioxythienyl)-N-dodecyl-carbazole)) (PBEDOT-NC12Cz)/carbon black Detector 3—A solution of poly(bis(2,7-(3,4-ethylenedioxythienyl)-N-dodecylcarbazole)) (PBEDOT-NC12Cz) was prepared by dissolving 50 mg of it into 20 ml of toluene. Fifty mg of Carbon black was then added and the solution was sonicated for approximately 10 minutes. Sensors were prepared by spin casting from this solution onto glass/gold substrates at a spin rate of 1000 rpm.

Poly (3-hexylthiophene)/Au

Detector 4—A solution of poly(3-hexylthiophene) was prepared by dissolving 50 mg of it into 20 ml of toluene. Films of the polymer were prepared on the sensor substrate by spin coating which involved saturating the substrate with polymer solution and spinning at 1000 rpm. The film was air dried and dipped once into a water solution of tetrachloroauric acid (0.5 g/20 ml) for five seconds. The film was then dipped immediately into a beaker of deionized water for washing. In this process, poly(3-hexylthiophene) is oxidized while the gold is reduced resulting in a conductive poly(3-hexylthiophene) containing gold salts as the counterion and Au (0) nanoparticles as the conductive filler.

Poly(3-hexylthiophene)/Pt

Detector 5—Similar to the procedure used for Poly(3-hexylthiophene)/Au above. A solution of poly(3-hexylthiophene) was prepared by dissolving 50 mg of it into 20 ml of toluene. Films of the polymer were prepared on the sensor substrate by spin coating which involved saturating the substrate with polymer solution and spinning at 1000 rpm. The film was air dried and dipped once into a water solution of hexachloroplatinum acid (0.5 g/20 ml) for five minutes. The film was then dipped immediately into a beaker of deionized water for washing. In this process, poly(3-hexylthiophene) is oxidized while the platinum is reduced resulting in a conductive poly(3-hexylthiophene) containing platinum salts as the counterion and Pt (0) nanoparticles as the conductive filler.

Charge Transfer Salts/Carbon Black

Detector 6—(a) A total weight of 0.2 g of a mixture of both Poly(N-vinylcarbazole) and tetracyanoquinoline (TCNQ) (in a 1:1 mole ratio) were dissolved into 20 ml of benzene. To this solution was added 50 mg of carbon black and the solution was sonicated for ten minutes. Sensors were prepared by saturating the solution onto a glass/gold substrate and spinning at a rate of 1000 rpm.

(b) A total weight of 0.2 g of a mixture of both Poly(N-vinylcarbazole) and 2,4,6-trinitrotoluene (TNT) (in a 1:1 mole ratio) were dissolved into 20 ml of benzene. To this solution was added 50 mg of carbon black and the solution was sonicated for ten minutes. Sensors were prepared by saturating the solution onto a glass/gold substrate and spinning at a rate of 1000 rpm.

Sensor Use: Exposures of Detectors 1, 2, and 3 to Various Analytes

Figure 12A:
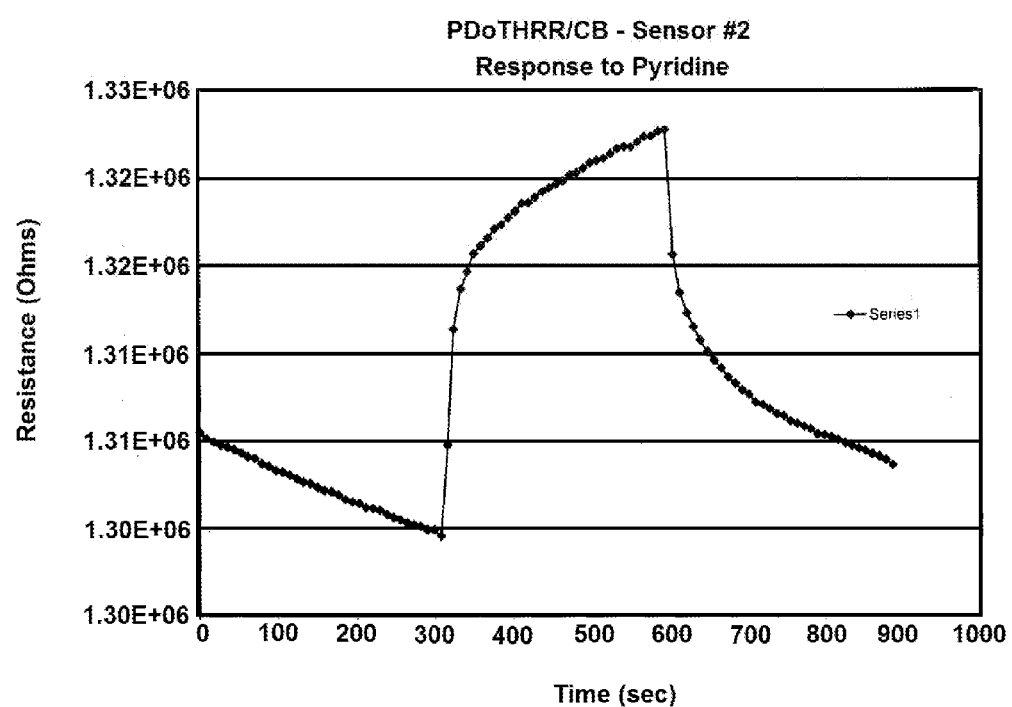
FIG. 12 shows the response to sensors in response to pyridine. (A) shows a response to pyridine in a poly(3-dodecylthiophene)/carbon black sensor. (B) shows a response to pyridine in a poly(3-hexylthiophene)/carbon black sensor. (C) shows a response to pyridine in a Poly(bis(2,7-(3,4-ethylenedioxythienyl)-N-dodecylcarbazole)) (PBEDOT-NC12Cz)/carbon black sensor.
Figure 12B:
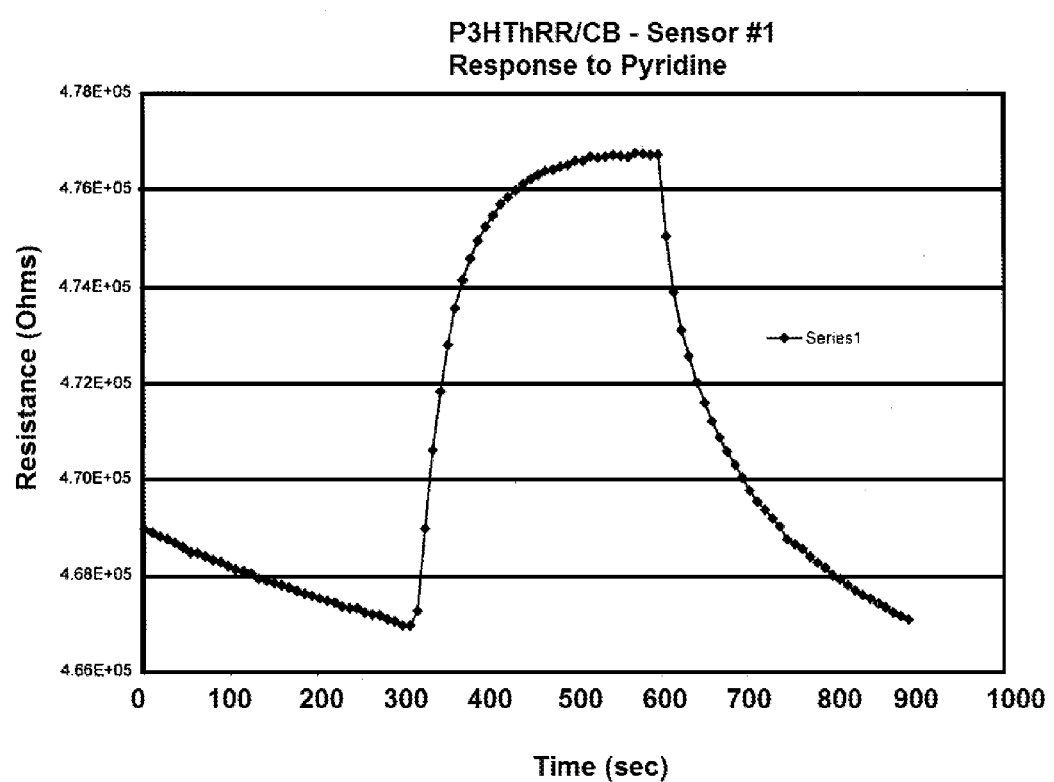
Figure 12C:
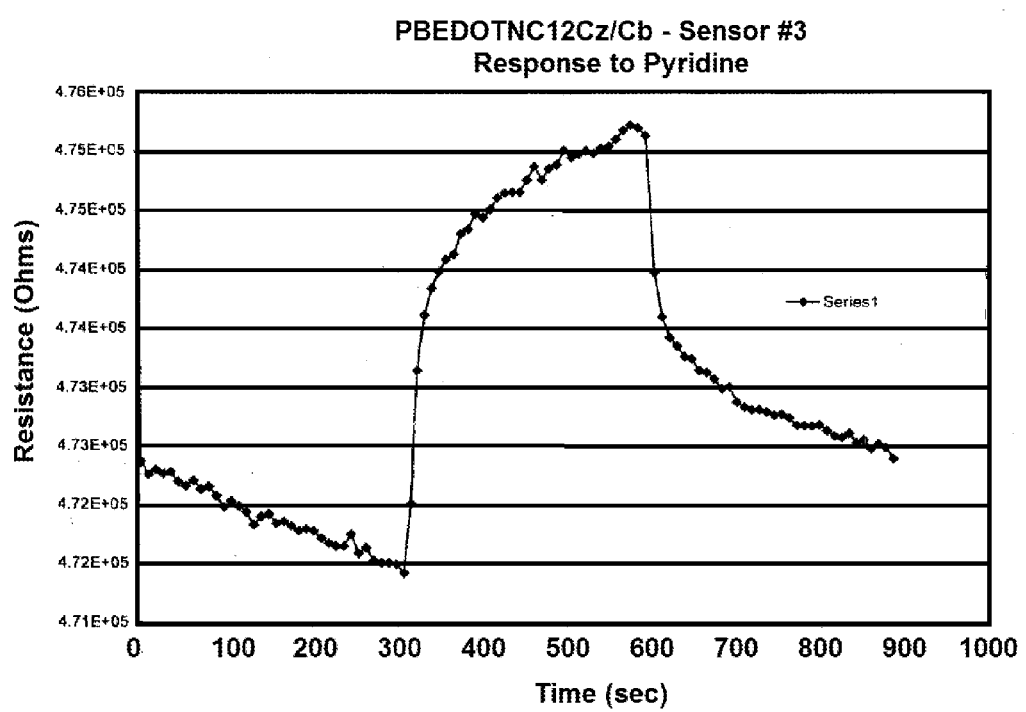

Detectors 1, 2, 3 were exposed to the following odorants at 0.5% of their saturated vapor pressure: Methanol, triethylamine, pyridine, quinoline, butylamine, ethylene diamine, aniline, and ethanol. FIG. 12 shows a representative response of detectors 1, 2, and 3 to pyridine.

Exposures of Detectors 4 and 5 to Different Analytes

Figure 13:
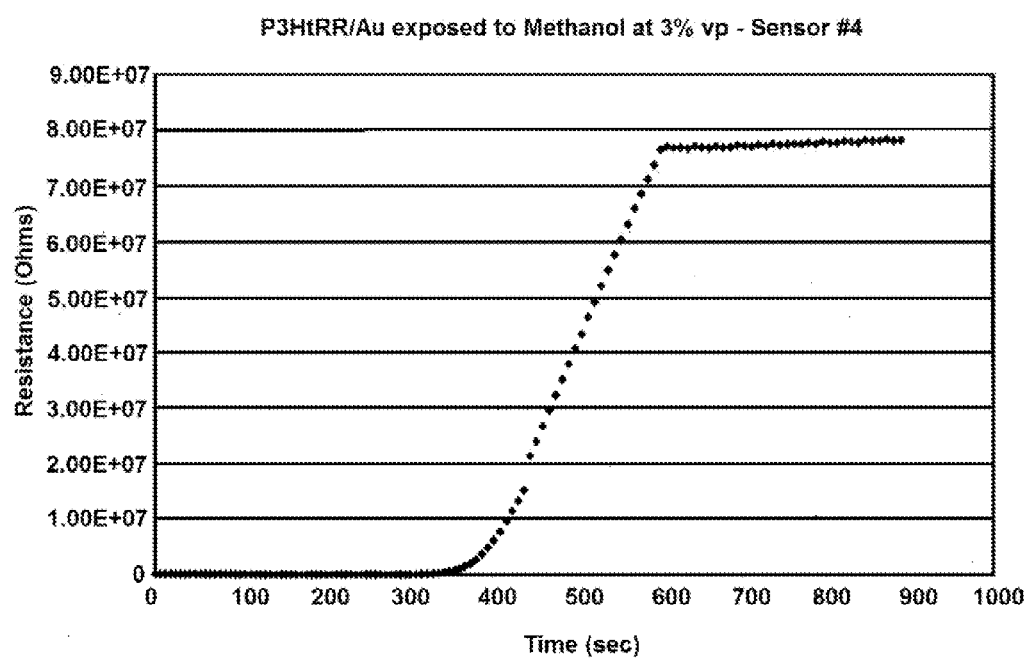
FIG. 13 shows a response to methanol in a poly(3-hexylthiophene)/Au sensor.
Figure 14:
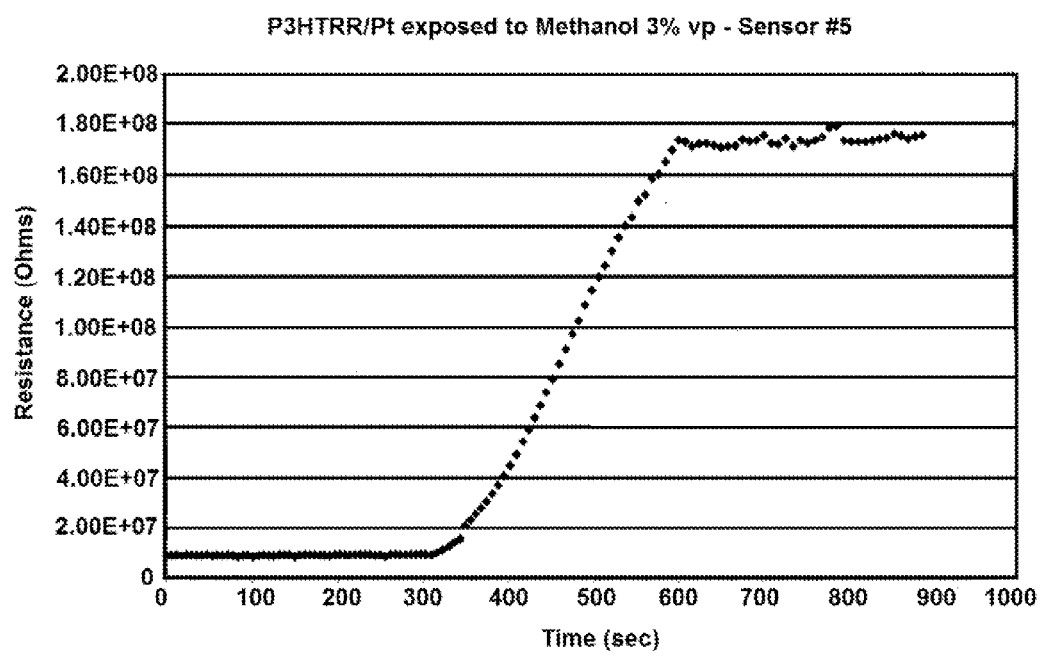
FIG. 14 shows a response to methanol in a poly(3-hexylthiophene)/Pt sensor.

Detectors 4 and 5 were exposed to the following analytes at 3% of their saturated vapor pressure; methanol, hexanethiol, toluene, acetonitrile, nitrotoluene, and chlorobenzene. Furthermore, they were exposed to triethyl amine and butylamine at 1% of their saturated vapor pressure. FIGS. 13 and 14 show representative response of detectors 4 and 5 to methanol.

Exposures of Detectors 6a and 6b to Different Analytes

Figure 15:
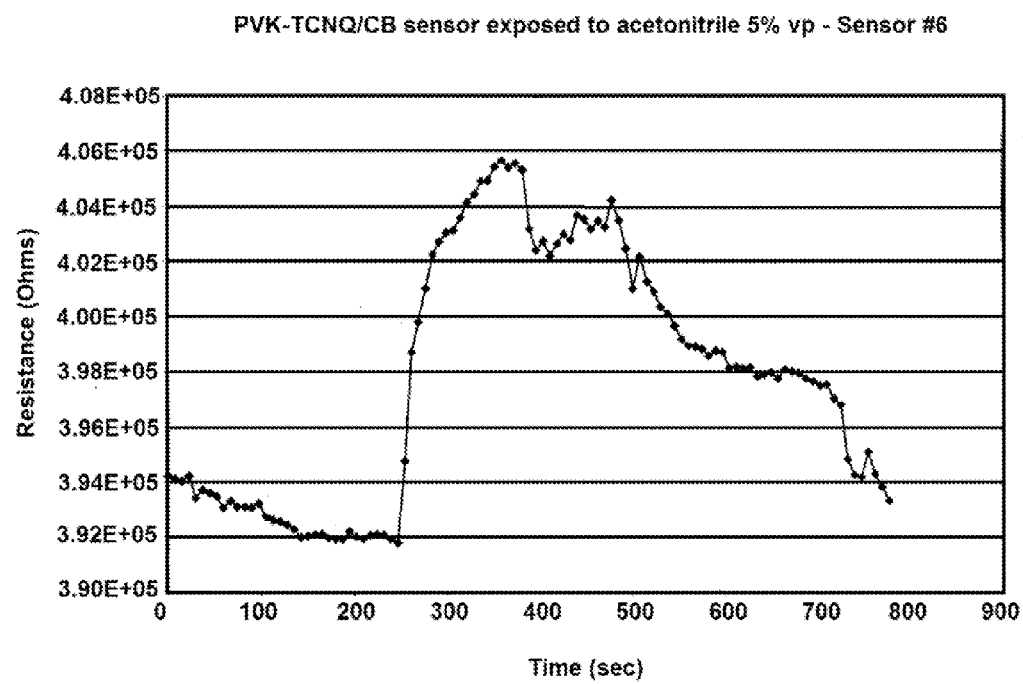
FIG. 15 shows a response to acetonitrile in a poly(N-vinylcarbazole)/tetracyanoquinoline (TCNQ) sensor (1:1).
Figure 16:
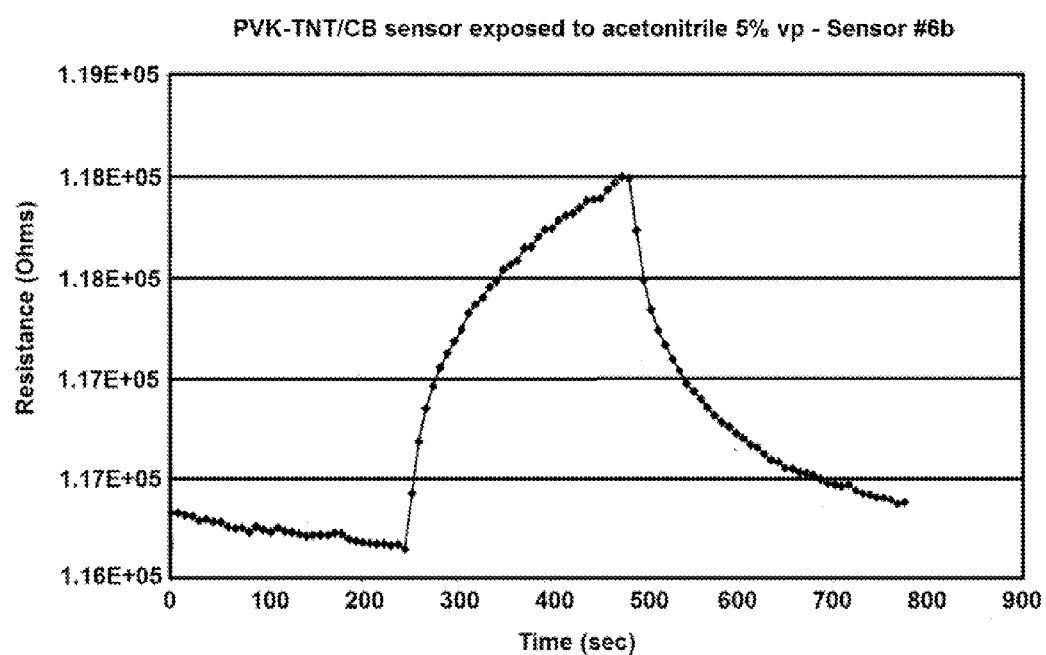
FIG. 16 shows a response to acetonitrile in a poly(N-vinylcarbazole)/2,4,6-trinitrotoluene (TNT) sensor (in a 1:1 mole ratio).

These sensors were exposed to the following analytes at 5% of their saturated vapor pressure; pyridine, acetonitrile, benzaldehyde, chlorobenzene, nitrobenzene, benzene, anisole, 3-nitrotoluene, nitromethane, ethanol, hexane, aniline, butylamine, α,α,α-trifluorotoluene, methanol and water. FIGS. 15 and 16 show the response of sensors 6a and 6b to acetonitrile.

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A sensor, comprising:
at least two conductive leads;
a sensing area comprising alternating regions of a doped or undoped conductive organic polymer material and an inorganic conductive material or carbon black disposed between, and in contact with, the at least two conductive leads, wherein the regions of inorganic conductive material or carbon black are separated by about 10-1000 angstroms, wherein the sensing area provides an electrical path through the regions of the conductive organic polymer material and the inorganic conductive material or carbon black, and wherein the sensing area is in direct contact with a vapor comprising an analyte to be detected, wherein the inorganic conductive material is selected from the group consisting of an inorganic conductor, and a mixed inorganic/organic conductor, wherein the inorganic conductor is a metal, a metal alloy, a metal oxide, a superconductor, or a combination thereof and wherein the inorganic conductor has an electrical conductivity that decreases as the temperature increase; and
an apparatus in electrical communication with the conductive leads for detecting a change in the sensing area between the at least two conductive leads when contacted with an analyte.

2. The sensor according to claim 1, wherein the conductive organic polymer material is selected from the group consisting of a polyaniline, an emeraldine salt of polyaniline, a polypyrrole, a polythiophene, a polyEDOT, and derivatives thereof.

3. The sensor according to claim 1, further comprising an insulator or plasticizer.

4. The sensor of claim 1, wherein the conductive organic polymer material is an emeraldine salt of polyaniline and the sensor comprises carbon black.

5. The sensor of claim 1, wherein the conductive organic polymer material is a doped polyaniline and the sensor comprises carbon black.

6. A sensor, comprising:
at least two conductive leads;
a sensing area comprising alternating interpenetrating regions of a doped or undoped conductive organic polymer material and an inorganic conductive material or carbon black disposed between and in contact with the at least two conductive leads, wherein the regions of inorganic conductive organic material or carbon black are separated by about 10-1000 angstroms, wherein the sensing area provides an electrical path through the regions of the conductive organic polymer material and the regions of the inorganic conductive material or carbon black, and wherein the sensing area is in direct contact with a vapor comprising an analyte to be detected, wherein the inorganic conductive material is selected form the group consisting of an inorganic conductor and a mixed inorganic/organic conductor, wherein the inorganic conductor is a metal, a metal alloy, a metal oxide, or a superconductor, or a combination thereof and wherein the inorganic conductor has an electrical conductivity that decreases as the temperature increases; and
an apparatus in electrical communication with the conductive leads for detecting a change in the sensing area between the at least two conductive leads when contacted with an analyte.

7. A sensor, comprising:
at least two conductive leads;
a sensing area comprising dispersed regions of a doped or undoped conductive organic polymer material and an inorganic conductive material or carbon black wherein the dispersed regions provide interpenetrating regions of the conductive organic polymer material and an inorganic conductive material or carbon black, wherein the regions of inorganic conductive material or carbon black are separated by about 10-1000 angstroms, the sensing area disposed between and in contact with the at least two conductive leads, wherein the sensing area provides an electrical path through the regions of the conductive organic polymer material and the regions of the inorganic conductive material or carbon black, and wherein the sensing area is in direct contact with a vapor comprising an analyte to be detected, wherein the inorganic conductive material is selected from the group consisting of an organic conductor, an organic complex, an inorganic conductor and a mixed inorganic/organic conductor, wherein the inorganic conductor is a metal, a metal alloy, a metal oxide, or a superconductor, or a combination thereof and wherein the inorganic conductor has an electrical conductivity that decreases as the temperature increases; and
an apparatus in electrical communication with the conductive leads for detecting a change in the sensing area between the at least two conductive leads when contacted with an analyte.

8. A sensor, comprising:
at least two conductive leads;
a sensing area comprising alternating interpenetrating regions of a doped or undoped polyaniline or an emeraldine salt of polyaniline and an inorganic conductive material disposed between, and in contact with, the at least two conductive leads, wherein the regions of the inorganic conductive material or carbon black are separated by about 10-1000 angstroms, wherein the sensing area provides an electrical path through the alternating interpenetrating regions of polyaniline or emeraldine salt of polyaniline and the inorganic conductive material; and
an apparatus in electrical communication with the conductive leads for detecting a change in the sensing area between the at least two conductive leads when contacted with an analyte.

9. The sensor of claim 8, wherein the inorganic conductive material is selected from the group consisting of an inorganic conductor, and a mixed inorganic/organic conductor, wherein the inorganic conductor is a metal, a metal alloy, a metal oxide, an oxidized metal, a superconductor, and any combination thereof.

10. A sensor array comprising:
a plurality of sensors, wherein at least one sensor comprises:
at least two conductive leads;
a sensing area comprising alternating interpenetrating regions of a doped or undoped conductive organic polymer material and an inorganic conductive material or carbon black disposed between an in contact with the at least two conductive leads, wherein the regions of inorganic conductive material or carbon black are separated by about 10-1000 angstroms, wherein the sensing area provides an electrical path through the alternating interpenetrating regions of the conductive organic polymer material and the regions of the inorganic conductive material or carbon black, wherein the sensing area is in direct contact with a vapor comprising an analyte to be detected, wherein the inorganic conductive material is selected from the group consisting of an an inorganic conductor and a mixed inorganic/organic conductor, wherein the inorganic conductor is a metal, a metal alloy, a metal oxide, or a superconductor, or a combination thereof and wherein the inorganic conductor has an electrical conductivity that decreases as the temperature increases.

11. The sensor array according to claim 10, wherein the sensor array comprises a plurality of sensors each comprising regions of a conductive organic polymer material and regions of an inorganic conductive material or carbon black wherein the conductive organic polymer material of at least one sensor is different from the conductive organic polymer material of at least one other sensor.

12. The sensor array according to claim 10, wherein the conductive organic polymer material is selected from the group consisting of a polyaniline, an emeraldine salt of polyaniline, a polypyrrole, a polythiophene, and a polyEDOT, and the inorganic conductive material is selected from the group consisting of Ag, Au, Cu, Pt, and AuCu.

13. The sensor array according to claim 10 or 12, further comprising a temperature control apparatus in thermal communication with at least one sensor.

14. The sensor array according to claim 10 or 12, further comprising an apparatus for detecting a change selected from the group consisting of resistance, conductance, impedance, and capacitance in the electrical properties of at least one sensor.

15. The sensor array according to claim 14, further comprising a temperature control apparatus in thermal communication with at least one sensor.

16. The sensor array according to claim 10, wherein the inorganic conductive material is selected from the group consisting of Ag, Au, Cu, Pt, and AuCu.

17. The sensor array according to claim 10, wherein the sensor comprises carbon black.

18. The sensor array according to claim 10, wherein the inorganic conductive material is a member selected from the group consisting of a metal, a metal alloy, a metal oxide, an organic complex, a superconductor, and a mixed inorganic/organic conductor.

19. The sensor array according to claim 10, wherein the inorganic conductive material is a particle.

20. The sensor array of claim 10, wherein the plurality of sensors comprise at least two conductive leads and a sensing area comprising alternating interpenetrating regions of a conductive organic polymer material and an inorganic conductive material or carbon black disposed between and in electrical communication with the at least two conductive leads.

21. The sensor array according to claim 20, wherein the conductive organic polymer material of one sensor of the plurality of sensors is compositionally different than at least one other sensor of the plurality of sensors.

22. A sensor array comprising:
a plurality of sensors, wherein at least one sensor comprises:
at least two conductive leads;
a sensing area comprising alternating interpenetrating regions of a doped or undoped conductive organic polymer material and an inorganic conductive material or carbon black disposed between, and in contact with, the at least two conductive leads, wherein the regions of inorganic conductive material or carbon black are separated by about 10-1000 angstroms, wherein the sensing area provides an electrical path through the regions of the conductive organic polymer material and the regions of the inorganic conductive material or carbon black, wherein the sensing area is in direct contact with a vapor comprising an analyte to bet detected, wherein the inorganic conductive material is selected form the group consisting of an inorganic conductor, and a mixed inorganic/organic conductor, wherein the inorganic conductor is a metal a metal alloy, a metal oxide, a superconductor, or a combination thereof, wherein the inorganic conductor has an electrical conductivity that decreases as the temperature increases; and
a measuring apparatus electrically coupled to the at least two conductive leads for detecting a change in the sensing area when contacted with an analyte.

23. A sensor array comprising:
a plurality of sensor wherein at least one sensor comprise alternating interpenetrating regions of a doped or undoped conductive organic polymer material and regions of an inorganic conductive material or carbon black wherein the sensors are in direct contact with a vapor comprising an analyte to be detected, wherein the regions of inorganic conductive material or carbon black are separated by about 10-1000 angstroms, wherein the inorganic conductive material is selected form the group consisting of an inorganic conductor, and a mixed inorganic/organic conductor, wherein the inorganic conductor is a metal a metal alloy, a metal oxide, a superconductor, or a combination thereof, wherein the inorganic conductor has an electrical conductivity that decreases as the temperature increases; and
means, electrically coupled to the plurality of sensors, for detecting a change in the plurality of sensors when contacted with an analyte.

24. A sensor array system comprising:
a plurality of sensors, wherein at least one sensor comprises:
at least two conductive leads;
a sensing area comprising alternating interpenetrating regions of a doped or undoped conductive organic polymer material and an inorganic conductive material or carbon black disposed between and in contact with the at least two conductive leads, wherein the regions of inorganic conductive material or carbon black are separated by about 10-1000 angstroms, wherein the sensing area provides an electrical path through the regions of the conductive organic polymer material and the regions of the inorganic conductive material or carbon black, wherein the sensing area is in direct contact with a vapor comprising an analyte to be detected, wherein the inorganic conductive material is selected from the group consisting of an inorganic conductor and a mixed inorganic/organic conductor, wherein the inorganic conductor is a metal, a metal alloy, a metal oxide, or a superconductor or a combination thereof and wherein the inorganic conductor has an electrical conductivity that decreases as the temperature increases;
a measuring apparatus that detects a change in the electrical properties of the at least one sensor, wherein at least one sensor is in communication with the measuring apparatus; and
a computer comprising a resident algorithm, wherein the computer processes the change in the electrical properties.

25. The sensor array system according to claim 24, wherein the measuring apparatus is an electrical measuring device.

26. The sensor array system according to claim 24, wherein the inorganic conductive material is an inorganic conductor.

27. The sensor array system according to claim 26, wherein the inorganic conductive material is a member selected from the group consisting of Ag, Au, Cu, Pt, and AuCu.

28. The sensor array system according to claim 24, wherein the plurality of sensors each comprise regions of a conductive organic polymer material and regions of an inorganic conductive material or carbon black.

29. The sensor array system according to claim 28, wherein the conductive organic polymer material of at least one sensor is different from the conductive organic polymer material of at least one other sensor.

30. The sensor array system according to claim 28, wherein the conductive organic polymer material of the plurality of sensors are compositionally the same.

31. The sensor array system according to claim 24, wherein the change in electrical properties is selected from the group consisting of impedance, conductance, capacitance, inductance, and resistance in the sensors.

32. The sensor array system according to claim 24, wherein the conductive organic polymer material is selected from the group consisting of a polyaniline, an emeraldine salt of polyaniline, a polypyrrole, a polythiophene, and a polyEDOT, and the inorganic conductive material is selected from the group consisting of Ag, Au, Cu, Pt, and AuCu.

33. The sensor array system according to claim 24 or 32, further comprising a temperature control apparatus in thermal communication with at least one sensor.

34. The sensor array system according to claim 14 or 32, wherein the change in electrical properties is a change in an electrical impedance.

35. The sensor array system according to claim 34, further comprising a temperature control apparatus in thermal communication with at least one sensor.

36. The sensor array system according to claim 24, wherein the sensor comprises carbon black.

37. The sensor array system according to claim 24, wherein the inorganic conductive material is selected from the group consisting of an organic conductor, an inorganic conductor, and a mixed inorganic/organic conductor.

38. The sensor array system according to claim 24, wherein the inorganic conductive is selected from the group consisting of a metal, a metal alloy, a metal oxide, a superconductor, and a mixed inorganic/organic conductor.

39. The sensor array system according to claim 24, wherein the inorganic conductive material is a particle.

40. The sensor array system according to claim 24, wherein each of the sensors comprises a conductive organic polymer material.

41. The sensor array system according to claim 24, wherein the resident algorithm is a member selected from the group consisting of principal component analysis, Fisher linear analysis, neural networks, genetic algorithms, fuzzy logic, pattern recognition, and combinations thereof.

42. A system for identifying a microorganism, the system comprising:
a measuring apparatus;
a sensor array comprising a plurality of sensors in communication with the measuring apparatus, wherein at least one sensor comprises:
at least two conductive leads;
a sensing area comprising alternating regions of a doped or undoped conductive organic polymer material and an inorganic conductive material or carbon black disposed between and in electrical communication with the at least two conductive leads, wherein the regions of inorganic conductive material or carbon black are separated by about 10-1000 angstroms, wherein the inorganic conductive material is selected form the group consisting of an inorganic conductor, and a mixed inorganic/organic conductor, wherein the inorganic conductor is a metal a metal alloy, a metal oxide, a superconductor, or a combination thereof, wherein the inorganic conductor has an electrical conductivity that decreases as the temperature increases, wherein the sensing area provides an electrical path through the regions of the conductive organic polymer material and the regions of the inorganic conductive material or carbon black, and wherein the sensing are is in direct contact with a vapor comprising a biomarker to be detected; and
a computer comprising a resident algorithm;
wherein the measuring apparatus is capable of detecting a response from each sensor in the array wherein the response are indicative of the presence of a biomarker of a microorganism and the computer is capable of assembling the responses into a response profile whereby the computer associates the response profile indicative of the biomarker with a microorganism for microorganism identification.

43. The system for identifying a microorganism in accordance with claim 42, wherein the resident algorithm of the computer is a member selected from the group consisting of principal component analysis, Fisher linear analysis, neural networks, genetic algorithms, fuzzy logic, pattern recognition, and combinations thereof.

44. The system for identifying a microorganism in accordance with claim 42, further comprising the steps of:
providing an information storage device coupled to the measuring apparatus; and
storing information in the information storage device.

45. The system for identifying a microorganism in accordance with claim 42, wherein the measuring apparatus includes a digital-analog converter.

46. A system for detecting an analyte in a sample, comprising:
a substrate having a plurality of sensors wherein at least one sensor comprises:
at least two conductive leads;
a sensing area comprising alternating interpenetrating regions of a doped or undoped conductive organic polymer material and an inorganic conductive material or carbon black disposed between, and in contact with, the at least two conductive leads, wherein the regions of inorganic conductive material or carbon black are separated by about 10-1000 angstroms, wherein the sensing area provides an electrical path through the regions of the conductive organic polymer material and the regions of the inorganic conductive material or carbon black such that the at least one sensor provides a response that varies according to the presence of an analyte in contact with it, wherein the sensing area is in direct contact with a vapor comprising an analyte to be detected, wherein the inorganic conductive material is selected form the group consisting of an inorganic conductor and a mixed inorganic/organic conductor, wherein the inorganic conductor is a metal, a metal alloy, a metal oxide, or a superconductor, or a combination thereof and wherein the inorganic conductor has an electrical conductivity that decreases as the temperature increases;
a detector operatively associated with the plurality of sensors, for measuring the response of the plurality of sensor when contacted with the sample;
a sample delivery unit for delivering the sample to be tested to the plurality of sensors; and
an information storage and processing device configured to store an ideal response for a predetermined analyte and to compare the response of the plurality of sensor with the stored ideal response, to detect the presence of the analyte in the sample.

47. The system in accordance with claim 46, wherein the information storage and processing device is configured to store ideal responses for a plurality of predetermined analytes; and
the information storage and processing device further is configured to compare the response of the plurality of sensors with the plurality of stored ideal responses, to detect the presence of each analyte in the sample.

48. The system in accordance with claim 46, wherein the sample is a liquid and the sample delivery unit comprises:
a flow passage interconnecting the substrate comprising the plurality of sensor with a mixture containing the liquid;
a gas-permeable, liquid-impermeable shield interposed in the flow passage; and
a device for extracting vapor from the liquid and for delivering the extracted vapor along the flow passage to the substrate comprising the plurality of sensors via the flow passage.

49. The system in accordance with claim 46, wherein the sample is gaseous and the sample delivery unit comprises:
a gas flow passage; and
a pump for pumping the gaseous sample to the substrate comprising the plurality of sensors via the gas flow passage.

50. The system in accordance with claim 46, wherein the sample is a vapor extracted from a solid and the sample delivery unit comprises:

a vapor flow passage; and a pump for pumping the vapor extracted from the solid to the substrate comprising the plurality of sensors via the vapor flow passage.

51. The system in accordance with claim 46, wherein the detector detects a member selected from the group consisting of electromagnetic energy, optical properties, resistance, capacitance, inductance, impedance, and combinations thereof.

52. The system in accordance with claim 46, wherein at least one other sensor I the plurality of sensors comprises a member selected from the group consisting of a surface acoustic wave sensor; a quartz microbalance sensor; a conductive composite; a chemiresistor; a metal oxide gas sensor; a conducting polymer sensor; a dye-impregnated polymer film on fiber optic detector; a polymer-coated micromirror; an electrochemical gas detector; a chemically sensitive field-effect transistor; a carbon black-polymer composite; a micro-electro-mechanical system device; and a micro-opto-electro-mechanical system device.

* * * * *

UNITED STATES PATENT AND TRADEMARK OFFICE
CERTIFICATE OF CORRECTION

PATENT NO.      : 8,394,330 B1
APPLICATION NO. : 09/409644
DATED           : March 12, 2013
INVENTOR(S)     : Church et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 years.

Signed and Sealed this
Second Day of June, 2015

Michelle K. Lee
*Director of the United States Patent and Trademark Office*